US011452801B2

(12) United States Patent
Plahey

(10) Patent No.: US 11,452,801 B2
(45) Date of Patent: Sep. 27, 2022

(54) MEASURING FLUID FLOW ASSOCIATED WITH A DIALYSIS MACHINE

(71) Applicant: Fresenius Medical Care Holdings, Inc., Waltham, MA (US)

(72) Inventor: Kulwinder S. Plahey, Martinez, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 570 days.

(21) Appl. No.: 16/674,703

(22) Filed: Nov. 5, 2019

(65) Prior Publication Data

US 2021/0128809 A1    May 6, 2021

(51) Int. Cl.
*A61M 1/16*    (2006.01)
*A61M 1/28*    (2006.01)
(Continued)

(52) U.S. Cl.
CPC ............ *A61M 1/1601* (2014.02); *A61M 1/14* (2013.01); *A61M 1/15* (2022.05); *A61M 1/152* (2022.05); *A61M 1/153* (2022.05); *A61M 1/154* (2022.05); *A61M 1/155* (2022.05); *A61M 1/156* (2022.05); *A61M 1/1524* (2022.05); *A61M 1/1561* (2022.05); *A61M 1/1621* (2014.02); *A61M 1/28* (2013.01); *A61M 1/308* (2014.02);
(Continued)

(58) Field of Classification Search
CPC .......... A61M 1/14; A61M 1/15; A61M 1/152; A61M 1/1524; A61M 1/153; A61M 1/154; A61M 1/155; A61M 1/156; A61M 1/1561; A61M 1/1601; A61M 1/1621; A61M 1/28; A61M 1/308; A61M 1/81; A61M 5/14; A61M 5/142; A61M 5/145; A61M 2205/3334; A61M 2205/123; A61M 2205/18; A61M 2205/3331; A61M 2205/3379; A61M 2205/36; A61M 2205/50; A61M 2205/702
See application file for complete search history.

(56) References Cited

U.S. PATENT DOCUMENTS 9,180,240 B2    11/2015    Farrell et al.
2011/0160649 A1    6/2011    Pan
(Continued)

OTHER PUBLICATIONS

International Patent Application No. PCT/US2020/058571, International Search Report (dated Feb. 4, 2021).

*Primary Examiner* — John Kim
(74) *Attorney, Agent, or Firm* — Leydig, Voit & Mayer, Ltd.

(57) ABSTRACT

A dialysis machine (e.g., a peritoneal dialysis (PD) machine) can include a control unit configured to monitor an amount of fluid withdrawn from a heater bag line during a PD treatment. A processor in the control unit is configured to operate a first pump to draw fluid into a first pump chamber and measure a first fluid volume in the first pump chamber. The processor is further configured to operate the first pump and a second pump to transfer fluid from the first pump chamber to a second pump chamber, measure a second fluid volume in the second pump chamber, and determine a measured fluid volume for a single pump cycle based on the first fluid volume and the second fluid volume. The first fluid volume is correlated to the second fluid volume and, therefore, the multiple independent measurements increase an accuracy of the fluid volume measurement.

20 Claims, 22 Drawing Sheets

(51) Int. Cl.

| | | |
|---|---|---|
| | *A61M 1/30* | (2006.01) |
| | *A61M 1/14* | (2006.01) |
| | *A61M 5/14* | (2006.01) |
| | *A61M 1/00* | (2006.01) |
| | *A61M 5/145* | (2006.01) |
| | *A61M 5/142* | (2006.01) |

(52) U.S. Cl.
CPC ................ *A61M 1/81* (2021.05); *A61M 5/14* (2013.01); *A61M 5/142* (2013.01); *A61M 5/145* (2013.01); *A61M 2205/123* (2013.01); *A61M 2205/18* (2013.01); *A61M 2205/3331* (2013.01); *A61M 2205/3334* (2013.01); *A61M 2205/3379* (2013.01); *A61M 2205/36* (2013.01); *A61M 2205/50* (2013.01); *A61M 2205/702* (2013.01)

(56) References Cited

U.S. PATENT DOCUMENTS

| | | |
|---|---|---|
| 2011/0196289 A1 | 8/2011 | Plahey et al. |
| 2014/0364800 A1 | 12/2014 | McGill et al. |
| 2019/0022296 A1 | 1/2019 | Ly et al. |
| 2019/0275228 A1 | 9/2019 | Crawford et al. |

MEASURING FLUID FLOW ASSOCIATED WITH A DIALYSIS MACHINE

BACKGROUND

Dialysis is a treatment used to support a patient with insufficient renal function. The two principal treatment options are hemodialysis (HD) and peritoneal dialysis (PD). During hemodialysis, the patient's blood is removed, e.g., via an arteriovenous (AV) fistula or other methods (e.g., AV graft), and passed through a dialyzer of a dialysis machine while also passing a dialysis solution, referred to as dialysate, through the dialyzer. A semi-permeable membrane in the dialyzer separates the blood from the dialysate within the dialyzer and facilitates the exchange of waste products (e.g., urea, creatine, potassium, etc.) between the blood stream and the dialysate. The membrane prevents the transfer of blood cells, protein, and other important components in the blood stream from entering the dialysate solution. The cleaned blood stream is then returned to the patient's body. In this way, the dialysis machine functions as an artificial kidney for cleaning the blood in patients with insufficient renal function.

In contrast with hemodialysis, the peritoneal dialysis treatment option pumps dialysate into a patient's peritoneal cavity, which is an area in the abdomen between the parietal peritoneum and visceral peritoneum (e.g., a space between the membrane that surrounds the abdominal wall and the membranes that surround the internal organs in the abdomen). The lining of the patient's peritoneum functions as a semi-permeable membrane that facilitates the exchange of waste product between the bloodstream and the dialysate, similar in function to the membrane in the dialyzer of the hemodialysis machine. The patient's peritoneal cavity is drained and filled with new dialysate over a number of PD cycles.

Automated PD machines, sometimes referred to as PD cyclers, are designed to control the PD treatment process so that it can be performed at home without clinical staff, typically while the patient sleeps overnight so as to minimize interference with the patient's life. The process is referred to as continuous cycler-assisted peritoneal dialysis (CCPD). Many PD cyclers are designed to automatically infuse, dwell, and drain dialysate to and from the peritoneal cavity. The PD treatment typically lasts several hours, often beginning with an initial drain phase to empty the peritoneal cavity of used or spent dialysate that was left in the peritoneal cavity at the end of the last PD treatment. The sequence then proceeds through a progression of fill, dwell, and drain phases that follow sequentially. A group of fill, dwell, and drain phases, in order, can be referred to as a PD cycle.

One aspect relevant to the operation of the PD cyclers is determining an amount of dialysate that has been processed by the machine to provide a rough estimate as to treatment progress. However, current methods of determining an amount of dialysate remaining in a dialysate bag may be subject to various inaccuracies.

SUMMARY

A system is provided for performing a dialysis treatment. In an embodiment, the dialysis system is a PD system. The PD system can include a plurality of pumps, a cassette, and a processor. The cassette includes a plurality of pump chambers, each pump chamber fluidly connected to a corresponding pressure chamber. The processor is configured to operate a first pump to draw fluid into a first pump chamber fluidly connected to a first pressure chamber and measure a first fluid volume in the first pump chamber. The processor is further configured to operate the first pump and a second pump to transfer fluid from the first pump chamber to a second pump chamber fluidly connected to a second pressure chamber, measure a second fluid volume in the second pump chamber, and determine a measured fluid volume for a single pump cycle based on the first fluid volume and the second fluid volume.

In an embodiment, each pump comprises a piston configured to engage with a corresponding pump chamber to increase or decrease a volume of the corresponding pump chamber. Measuring a fluid volume in the corresponding pump chamber is performed by extending the piston to decrease the volume in the corresponding pump chamber, monitoring a pressure signal from a pressure transducer configured to measure a fluid pressure in the corresponding pressure chamber, reading a position of the piston at a time indicated by the pressure signal, and converting the position of the piston into the measured fluid volume.

In an embodiment, determining the measured fluid volume for the single pump cycle is performed by determining a difference between the first fluid volume and the second fluid volume, comparing the difference to a threshold value, and, if the difference is below the threshold value, calculating a mean of the first fluid volume and the second fluid volume as the measured fluid volume, or, if the difference is above the threshold value, setting an alert.

In an embodiment, fluid is drawn from a heater bag line coupled to the cassette. The processor is further configured to accumulate the measured fluid volume in a total fluid volume variable to monitor a total amount of fluid drawn from the heater bag line, determine that the total amount of fluid drawn from the heater bag line is above a threshold value, and configure the cassette to withdraw fluid from a second line to transfer additional fluid to the heater bag line.

In some embodiments, a method for measuring fluid flow through a PD cycler is performed by operating a first pump to draw fluid into a first pump chamber of a cassette, measuring a first fluid volume in the first pump chamber, operating the first pump and a second pump to transfer fluid from the first pump chamber to a second pump chamber of the cassette, measuring a second fluid volume in the second pump chamber, and comparing the first fluid volume to the second fluid volume to determine a measured fluid volume for a single pump cycle. A computer readable storage medium storing instructions for performing the method above is also disclosed.

In an embodiment, the plurality of pumps can include at least three pumps. In such an embodiment, the processor can be further configured to operate the second pump and a third pump to transfer fluid from the second pump chamber to a third pump chamber fluidly connected to a third pressure chamber, measure a third fluid volume in the third pump chamber, and calculate a mean of the first fluid volume, the second fluid volume, and the third fluid volume as the measured fluid volume.

DETAILED DESCRIPTION

Figure 1:
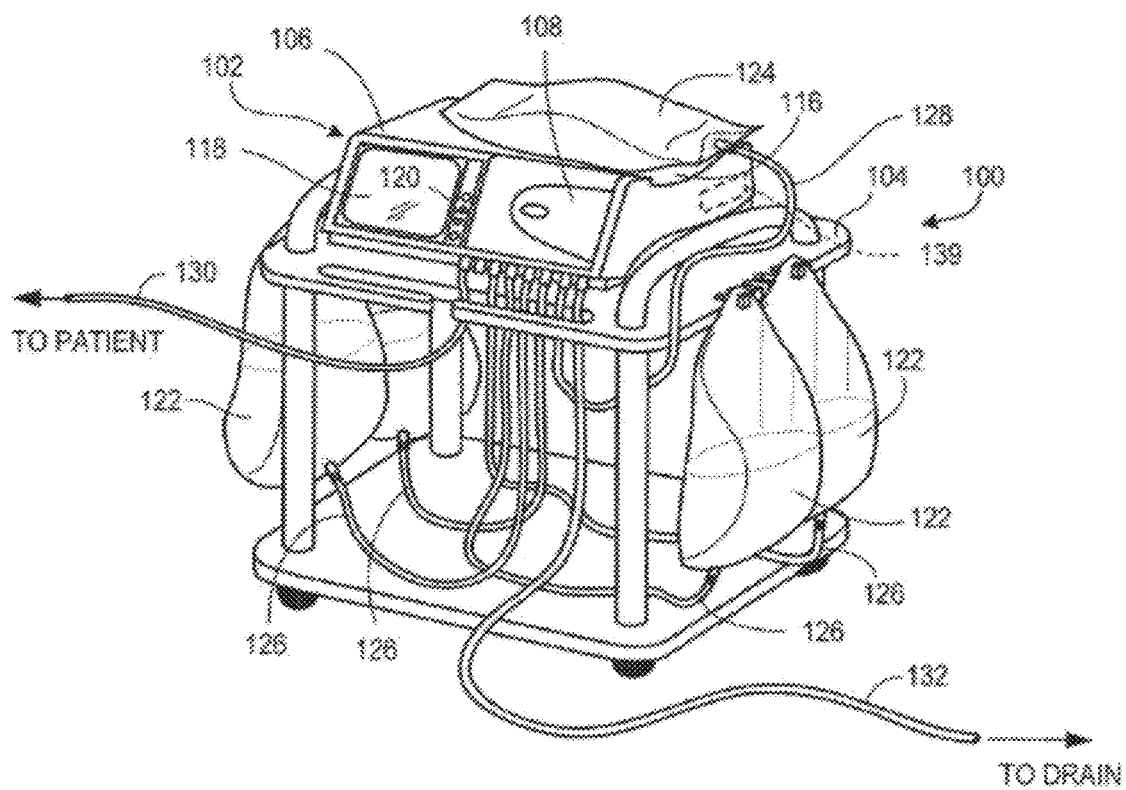
FIG. 1 illustrates a peritoneal dialysis (PD) system, in accordance with some embodiments.

A peritoneal dialysis (PD) machine can be designed to measure an amount of fluid drained from a dialysate bag in order to detect when a source of dialysate may be getting low. This information can be used to pause a PD treatment while a patient or caregiver changes the dialysate bag, set an alert of the PD cycler, or fill a heater bag with reserve fluid from an alternate dialysate bag connected to the PD cycler.

A conventional technique for measuring an amount of fluid that remained in a heater bag uses load cells positioned under a tray designed to hold the heater bag. The load cells generate signals that are translated into a weight of the tray plus heater bag. The weight can be used to infer how much fluid is in the heater bag, given that the weight of the tray and the weight of the heater bag without fluid remains constant. However, this technique has limitations. First, there is no way to prevent a caregiver or patient from placing additional weight on the tray while the PD treatment is active. For example, a patient could place a book or other item on top of the tray during treatment, which could cause the PD cycler to infer an incorrect amount of dialysate in the heater bag. Second, given the low confidence that the measured weight represents the actual amount of dialysate on the tray, as opposed to weight from foreign objects on the tray, the measured weight cannot be used for any vital operations of the PD cycler that rely on knowing the amount of fluid in the heater bag. Thus, the utility of this information currently may be limited to setting alerts to inform the caregiver/patient that the dialysate bag may need to be replaced.

The load cells are costly to implement in the PD cycler and, as discussed above, provide information of limited utility due to the inability to ensure the accuracy of the information. Therefore, a new PD cycler may omit the load cells in order to reduce the cost of the PD cycler. One technique to monitor the amount of fluid in the heater bag, indirectly, is to monitor an amount of fluid that has been pumped from the heater bag. By subtracting a volume of dialysate that has been pumped out of the heater bag, and knowing the volume of fluid contained in the heater bag initially, an estimate of the volume of fluid that remains in the heater bag can be calculated. The accuracy of the estimate depends on the accuracy of measuring the fluid volume being withdrawn from the heater bag.

One technique for measuring the volume of fluid pumped out of the heater bag uses the volume of the pump chambers of the cassette and pressure transducers that measure a fluid pressure in the pump chambers of the cassette. A combination of a position of a piston head attached to a membrane of the pump chamber and a signal that represents the fluid pressure in the pump chamber can be utilized to estimate a volume of fluid within the pump chamber after each stroke of the piston. Consequently, the PD cycler measures, indirectly, a volume of the fluid passing through the pump chamber for each stroke of the piston. One way to improve the accuracy of this measurement is to pass the same volume through multiple pump chambers, thereby taking multiple measurements using different pressure transducer signals and pistons. A combination of the multiple independent measurements can be used to estimate the fluid volume to a high degree of accuracy, which can be used to replace the functionality of the conventional load cell measurements of legacy PD cyclers.

FIG. 1 illustrates a peritoneal dialysis (PD) system 100, in accordance with some embodiments. The PD system 100 can include a PD machine 102, which can alternately be referred to as a PD cycler, seated on a cart 104. The PD machine 102 includes a housing 106, a door 108, and a cassette interface 110 that contacts a disposable PD cassette 112 when the cassette 112 is disposed within a cassette compartment 114 formed between the cassette interface 110 and the closed door 108. The cassette compartment 114, cassette interface 110, and cassette 112 are shown in more detail in FIG. 2. A heater tray 116 is positioned on top of the housing 106. The heater tray 116 is sized and shaped to accommodate a bag of PD solution such as dialysate (e.g., a 5 liter bag of dialysate). The PD machine 102 also includes a user interface such as a touch screen display 118 and additional control buttons 120 that can be operated by a user (e.g., a caregiver or a patient) to allow, for example, set up, initiation, and/or termination of a PD treatment. The system and techniques described herein are discussed principally in connection with a specific type of PD machine. However, it is noted that the system and techniques described herein may be used in connection with other types of PD machines and/or other dialysis machines or medical devices having cassettes and pump chambers, and for which measuring fluid flow therein would be desirable.

Dialysate bags 122 are suspended from fingers on the sides of the cart 104, and a heater bag 124 is positioned in the heater tray 116. The dialysate bags 122 and the heater bags 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient's peritoneal cavity during use. The catheter may be surgically implanted in the patient and connected to the patient line 130 via a port, such as a fitting, prior to the PD treatment. The drain line 132 can be connected to a drain or drain receptacle and can be used to pass dialysate from the cassette 112 to the drain or drain receptacle during use.

The PD machine 102 also includes a control unit 139 (e.g., a processor, controller, system-on-chip (SoC), or the like). The control unit 139 can receive signals from and transmit signals to the touch screen display 118, the control panel 120, and the various other components of the PD system 100. The control unit 139 can control the operating parameters of the PD machine 102. In some embodiments, the control unit 139 includes an MPC823 PowerPC device manufactured by Motorola, Inc. The control unit 139 may further include one or more network communication components or transceivers for communication with peripheral devices (e.g., blood pressure cuff, weight scale, smartphone, etc.) over a short-range wireless network, such as a WiFi or Bluetooth network, and/or with an external network (e.g., via the Internet), and such communication may be facilitated by communication with one or more network devices, such as a gateway device located in the home with the PD machine 102.

Figure 2:
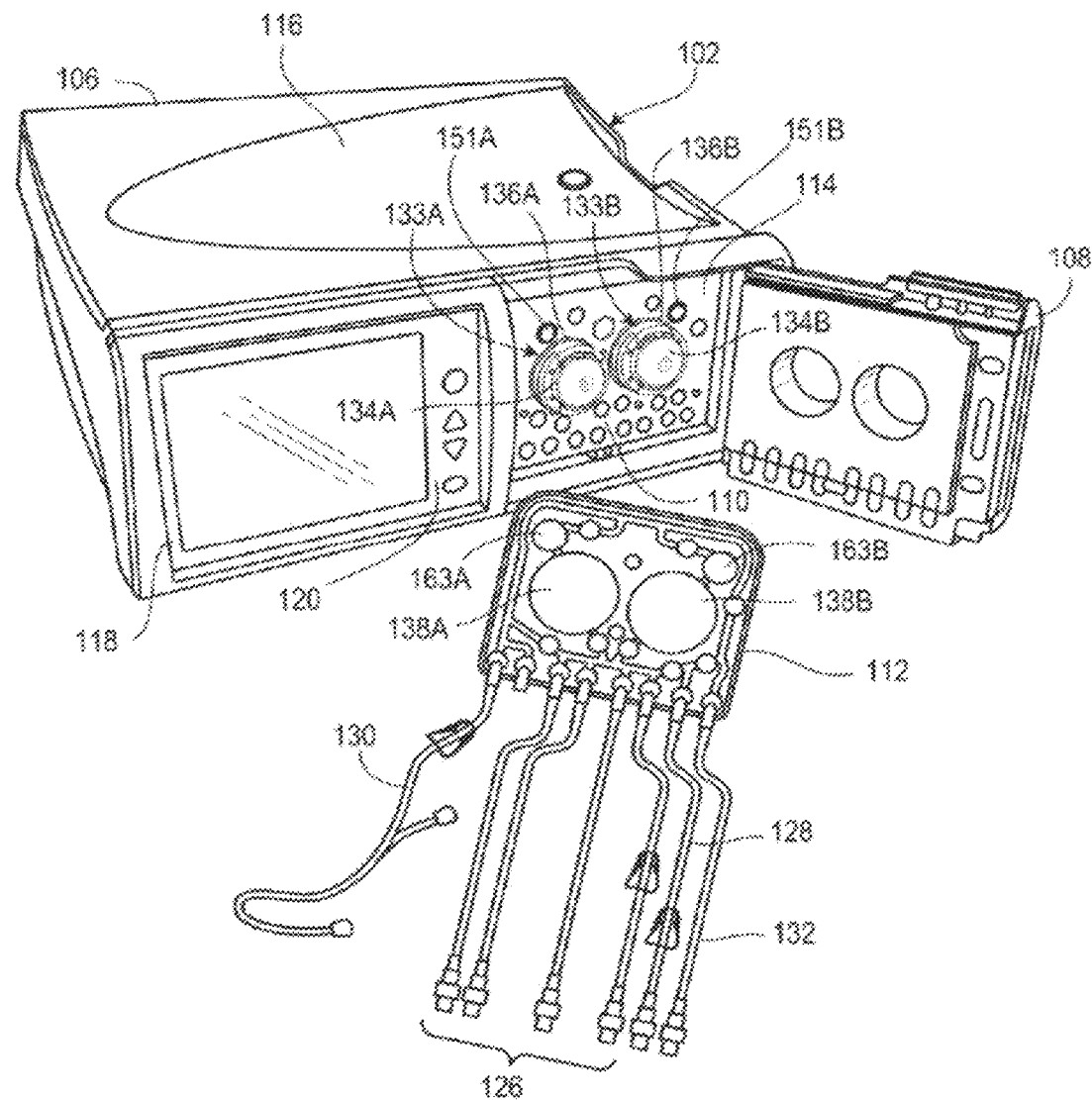
FIG. 2 is a perspective view of the PD machine and the PD cassette of the PD system of FIG. 1, in accordance with some embodiments

FIG. 2 is a perspective view of the PD machine 102 and the PD cassette 112 of the PD system 100 of FIG. 1, in accordance with some embodiments. As depicted in FIG. 2, the PD cassette 112 is placed proximate the cassette interface 110. The cassette 112 contains pump chambers 138A, 138B, pressure sensing chambers 163A, 163B, and valve chambers for controlling the flow of fluid through the cavities of the cassette 112. The cassette 112 is connected to the dialysate bag lines 126, the heater bag line 128, the patient line 130, and the drain line 132.

The cassette interface 110 includes a surface having holes formed therein. The PD machine 102 includes pistons 133A, 133B with piston heads 134A, 134B attached to piston shafts. The piston shafts can be actuated to move the piston heads 133A, 133B axially within piston access ports 136A, 136B formed in the cassette interface 110. The pistons 133A, 133B are sometimes referred to herein as pumps. In some embodiments, the piston shafts can be connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward on the lead screws. The stepper motors can be controlled by driver modules. The nuts, in turn, are connected to the piston shafts, which cause the piston heads 134A, 134B to move axially inward and outward as the stepper motors drive the lead screws. Stepper motor controllers provide the necessary current to be driven through the windings of the stepper motors to move the pistons 133A, 133B. The polarity of the current determines whether the pistons 133A, 133B are advanced or retracted. In some embodiments, the stepper motors require 200 steps to make a full rotation, and this corresponds to 0.048 inches of linear travel of the piston heads 134A, 134B.

In some embodiments, the PD system 100 also includes encoders (e.g., optical quadrature encoders) that measure the rotational movement and direction of the lead screws. The axial positions of the pistons 133A, 133B can be determined based on the rotational movement of the lead screws, as indicated by feedback signals from the encoders. Thus, measurements of the position calculated based on the feedback signals can be used to track the position of the piston heads 134A, 134B of the pistons 133A, 133B.

When the cassette 112 is positioned within the cassette compartment 114 of the PD machine 102 with the door 108 closed, the piston heads 134A, 134B of the PD machine 102 align with the pump chambers 138A, 138B of the cassette 112 such that the piston heads 134A, 134B can be mechanically connected to dome-shaped fastening members of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B. Retraction of the piston heads 134A, 134B away from the cassette 112 can increase the volume of the pump chambers 138A, 138B and cause dialysate to be drawn into the pump chambers 138A, 138B.

The cassette 112 also includes pressure sensor chambers 163A, 163B. When the cassette 112 is positioned within the cassette compartment 114 of the PD machine 102 with the door 108 closed, pressure sensors 151A, 151B align with the pressure sensor chambers 163A, 163B. Portions of a membrane that overlies the pressure sensor chambers 163A, 163B adhere to the pressure sensors 151A, 151B using vacuum pressure. Specifically, clearance around the pressure sensors 151A, 151B communicates vacuum to the portions of the cassette membrane overlying the pressure sensing chambers 163A, 163B to hold those portions of the cassette membrane tightly against the pressure sensors 151A, 151B. The pressure of fluid within the pressure sensing chambers 163A, 163B causes the portions of the cassette membrane overlying the pressure sensor chambers 163A, 163B to contact and apply a force to the pressure sensors 151A, 151B.

The pressure sensors 151A, 151B can be any sensors that are capable of measuring the fluid pressure in the pressure sensor chambers 163A, 163B. In some embodiments, the pressure sensors are solid state silicon diaphragm infusion pump force/pressure transducers. One example of such a sensor is the model 1865 force/pressure transducer manufactured by Sensym® Foxboro ICT. In some embodiments, the force/pressure transducer is modified to provide increased voltage output. The force/pressure transducer can, for example, be modified to produce an output signal of 0 to 5 volts.

Figure 3:
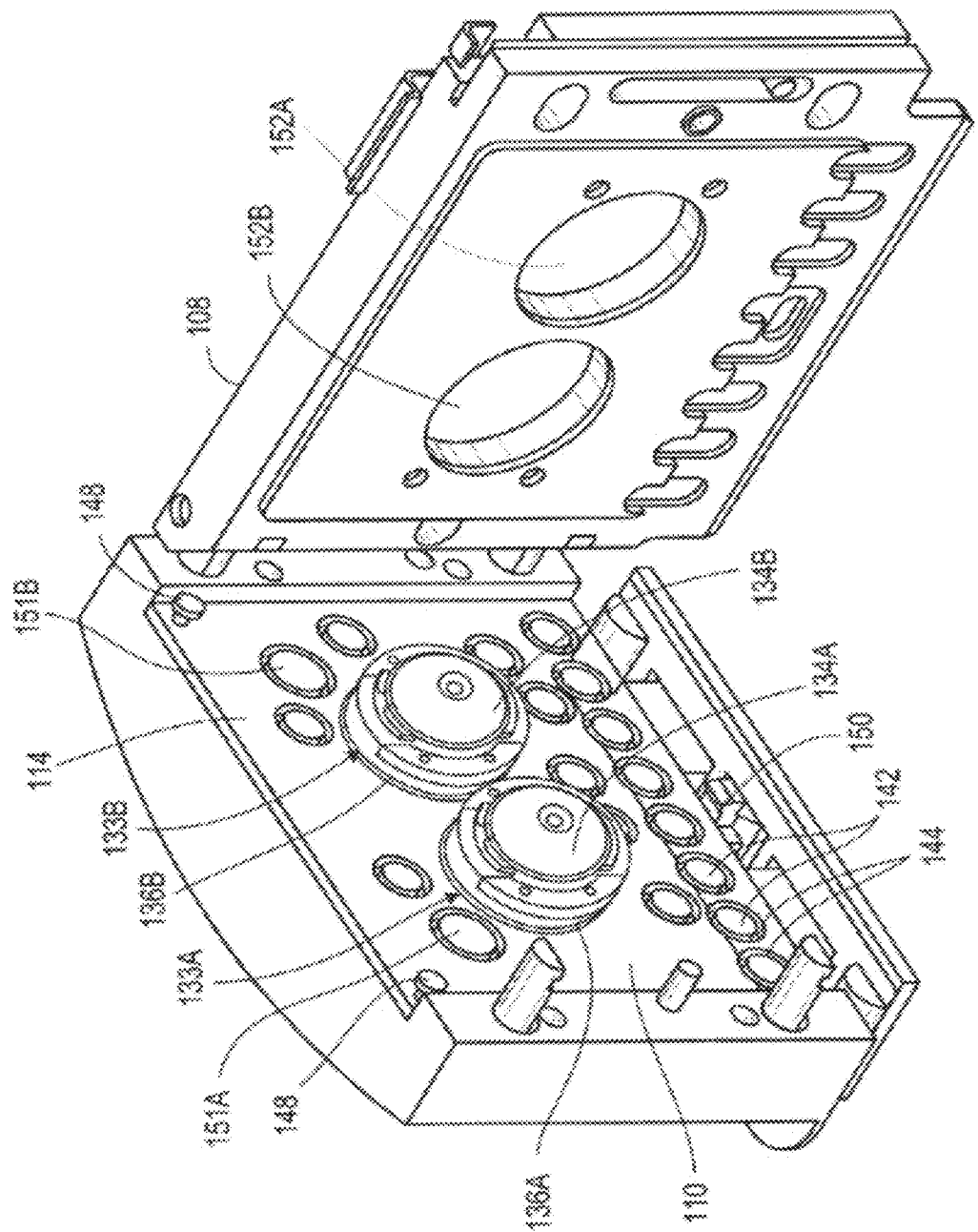
FIG. 3 is a perspective view of an open cassette compartment of the PD machine of FIG. 1, in accordance with some embodiments.

FIG. 3 is a perspective view of an open cassette compartment 114 of the PD machine 102 of FIG. 1, in accordance with some embodiments. As discussed above, the PD machine 102 includes pistons 133A, 133B disposed in piston access ports 136A, 136B, respectively. The PD machine 102 also includes multiple inflatable members 142 positioned within inflatable member ports 144 in the cassette interface 110. The inflatable members 142 align with depressible dome regions of the cassette 112 when the cassette 112 is positioned within the cassette compartment 114 of the PD machine 102. While only a couple of the inflatable members 142 are labeled in FIG. 3, it should be understood that the PD machine 102 includes an inflatable member 142 associated with each of the depressible dome regions of the cassette 112. The inflatable members 142 act, in cooperation with the depressible dome regions, as valves to direct dialysate through the cassette 112 in a desired manner during use. In particular, the inflatable members 142 bulge outward beyond the surface of the cassette interface 110 and into contact with the depressible dome regions of the cassette 112 when inflated, and retract into the inflatable member ports 144 and out of contact with the cassette 112 when deflated. By inflating certain inflatable members 142 to depress their associated dome regions on the cassette 112, certain fluid flow paths within the cassette 112 can be occluded. Thus, dialysate can be pumped through the cassette 112 by actuating the piston heads 134A, 134B, and can be guided along desired flow paths within the cassette 112 by selectively inflating and deflating the various inflatable members 142.

In some embodiments, locating pins 148 extend from the cassette interface 110 of the PD machine 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112. The locating pins 148 help to ensure that proper alignment of the cassette 112 within the cassette compartment 114 is maintained during use.

The door 108 of the PD machine 102 defines cylindrical recesses 152A, 152B that substantially align with the pistons 133A, 133B when the door 108 is in the closed position. When the cassette 112 is positioned within the cassette compartment 114 with the door 108 closed, the pump chambers 138A, 138B at least partially fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the surface of the pump chambers 138A, 138B, and the other portions of the door 108 support the other regions or surfaces of the cassette 112. The door 108 can counteract the forces applied by the inflatable members 142 and, therefore, allows the inflatable members 142 to actuate the depressible dome regions on the cassette 112. The engagement between the door 108 and the cassette 112 can also help to hold the cassette 112 in a desired position within the cassette compartment 114 to further ensure that the pistons 133A, 133B align with the fluid pump chambers 138A, 138B of the cassette 112.

The control unit 139 of FIG. 1 is connected to the pressure sensors 151A, 151B, to the stepper motors (e.g., the drivers for the stepper motors) that drive the pistons 133A, 133B, and to the encoders that monitor rotation of the lead screws attached to the stepper motors such that the control unit 139 can receive signals from and transmit signals to those components of the PD system 100. The control unit 139 monitors the components to which it is connected to determine whether any complications exist within the PD system 100, such as the presence of an occlusion or blockage in the patient line 130.

Figure 4:
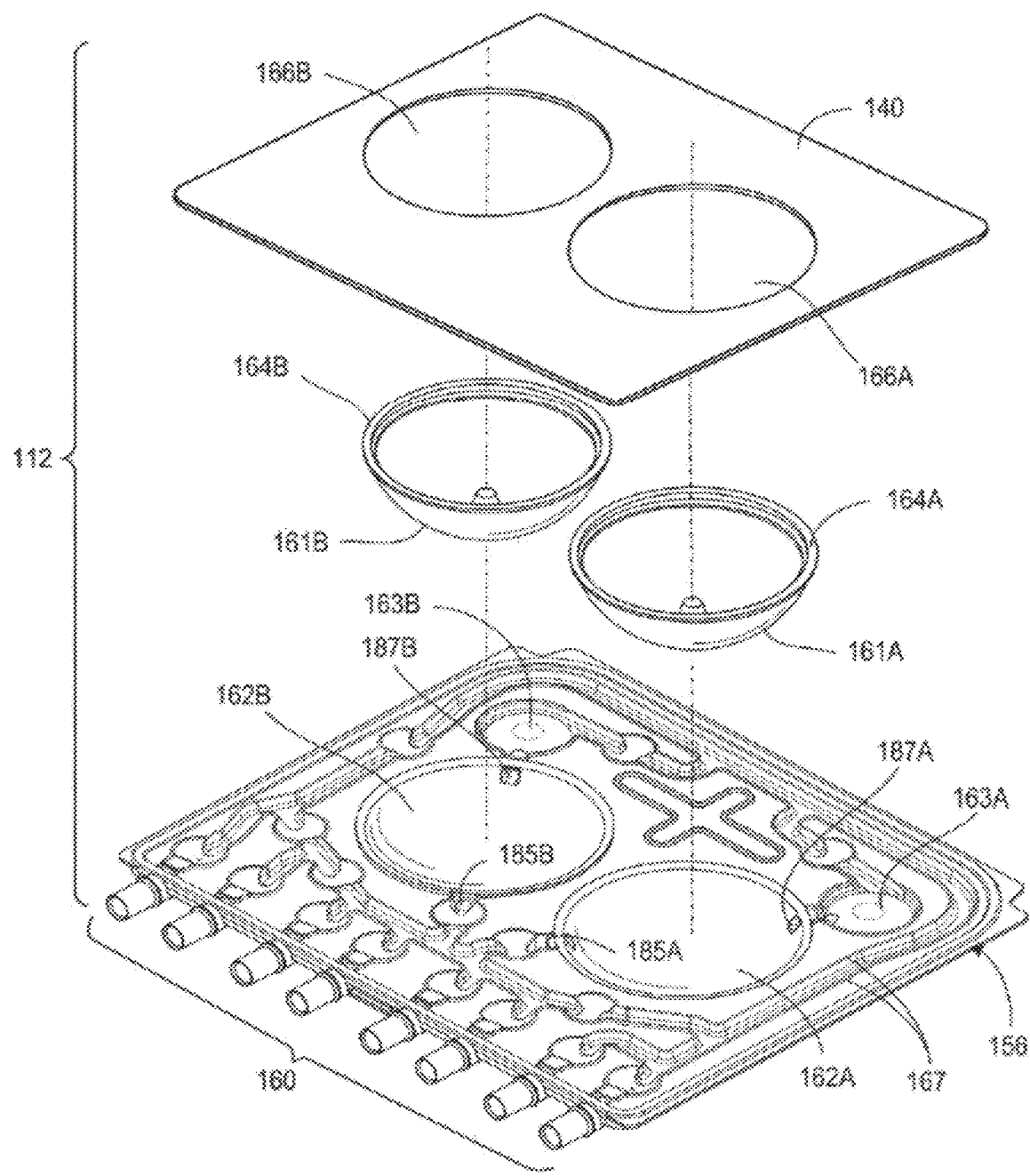
FIG. 4 is an exploded, perspective view of the PD cassette of FIG. 2, in accordance with some embodiments.
Figure 5:
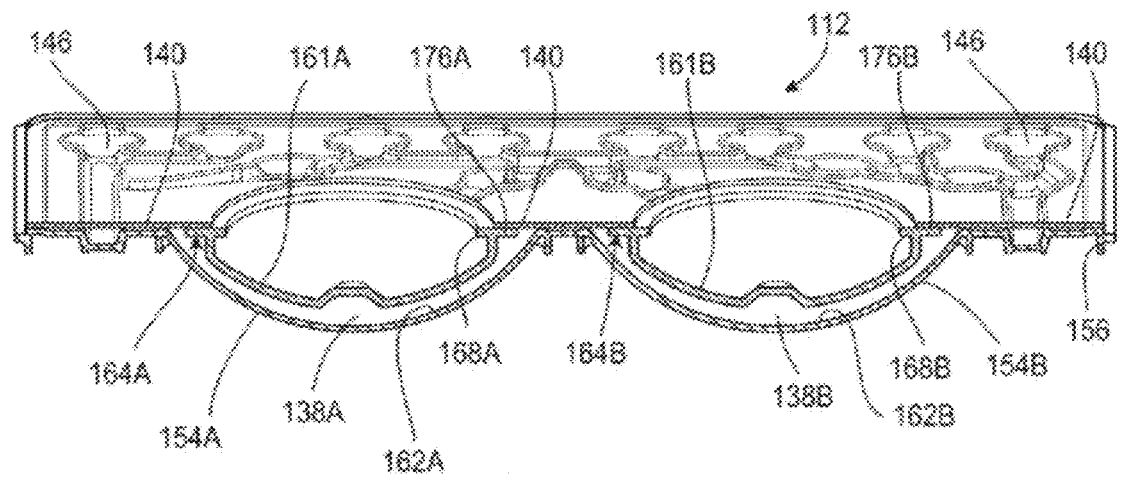
FIG. 5 is a cross-sectional view of the fully assembled PD cassette of FIG. 2, in accordance with some embodiments.
Figure 6:
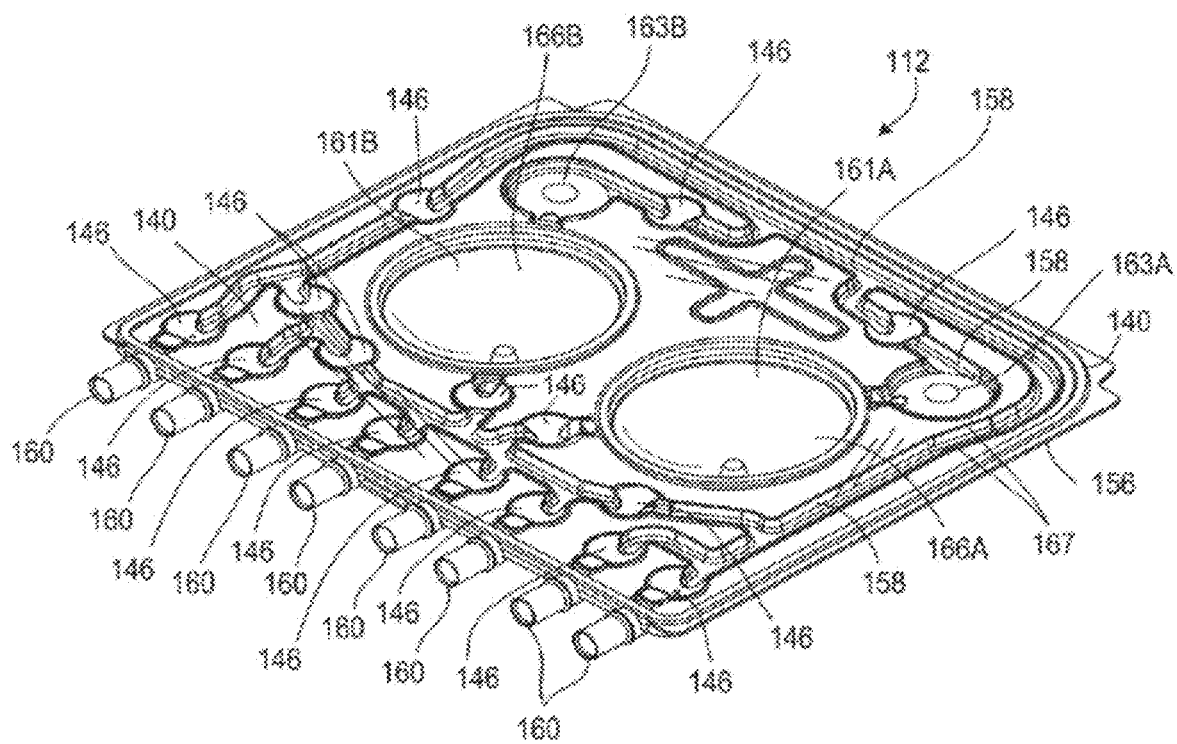
FIGS. 6 and 7 are perspective views of the PD cassette of FIG. 2 from a front side and a back side, respectively, in accordance with some embodiments.
Figure 7:
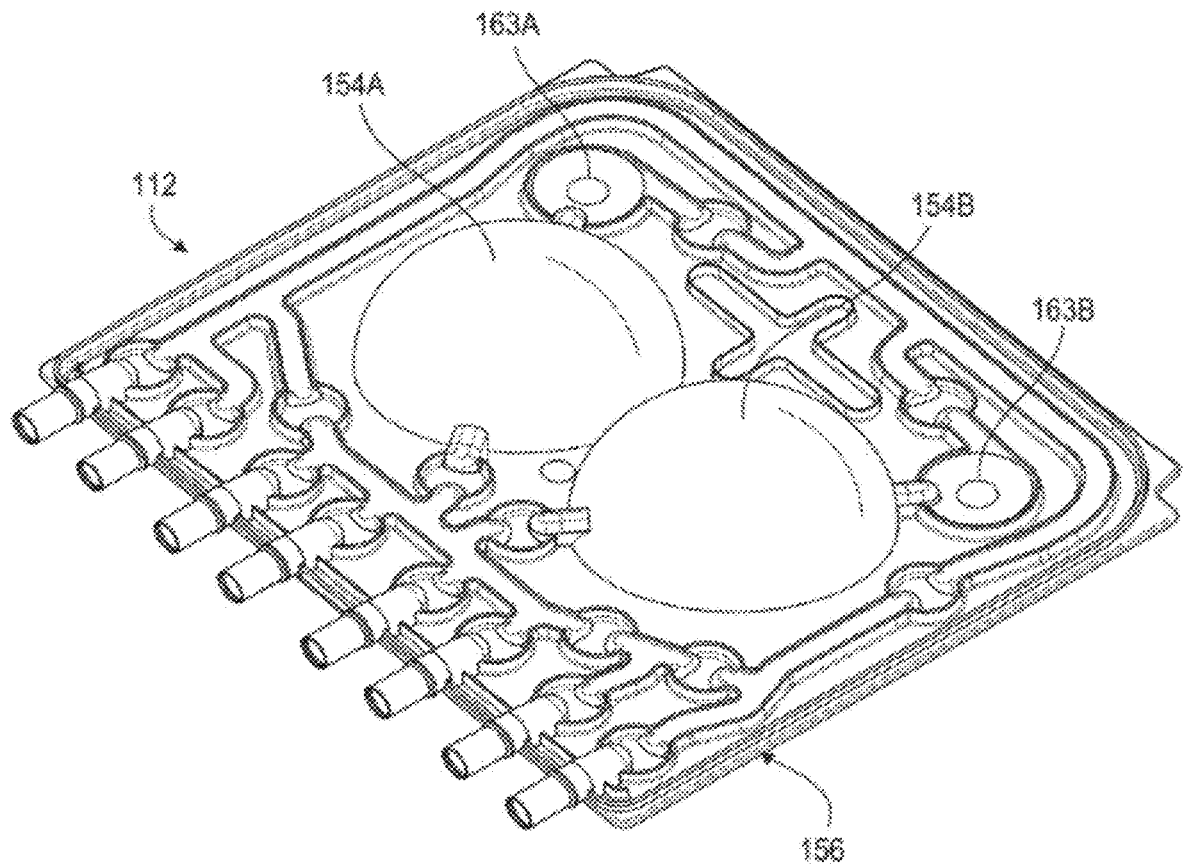

FIG. 4 is an exploded, perspective view of the PD cassette 112 of FIG. 2, in accordance with some embodiments. FIG. 5 is a cross-sectional view of the fully assembled PD cassette 112 of FIG. 2, in accordance with some embodiments. FIGS. 6 and 7 are perspective views of the PD cassette 112 of FIG. 2 from a front side and a back side, respectively, in accordance with some embodiments.

As depicted in FIGS. 4-7, the PD cassette 112 includes a flexible membrane 140 that is attached to a periphery of a tray-like rigid base 156. Rigid dome-shaped fastening members 161A, 161B are positioned within recessed regions 162A, 162B of the base 156. The dome-shaped fastening members 161A, 161B are sized and shaped to receive the piston heads 134A, 134B of the PD machine 102. In some embodiments, the dome-shaped fastening members 161A, 161B have a diameter, measured from the outer edges of annular flanges 164A, 164B, of about 1.5 inches to about 2.5 inches (e.g., about 2.0 inches) and take up about two-thirds to about three-fourths of the area of the recessed regions 162A, 162B. The annular flanges 164A, 164B of the rigid dome-shaped fastening members 161A, 161B are attached in a liquid-tight manner to portions of the inner surface of the membrane 140 surrounding substantially circular apertures 166A, 166B formed in the membrane 140. The annular flanges 164A, 164B of the rigid dome-shaped fastening members 161A, 161B can, for example, be thermally bonded or adhesively bonded to the membrane 140. The apertures 166A, 166B of the membrane 140 expose the rigid dome-shaped fastening members 161A, 161B such that the piston heads 134A, 134B are able to directly contact and mechanically connect to the dome-shaped fastening members 161A, 161B during use.

The annular flanges 164A, 164B of the dome-shaped fastening members 161A, 161B form annular projections 168A, 168B that extend radially inward and annular projections 176A, 176B that extend radially outward from the side walls of the dome-shaped fastening members 161A, 161B. When the piston heads 134A, 134B are mechanically connected to the dome-shaped fastening members 161A, 161B, the radially inward projections 168A, 168B engage the rear angled surfaces of the sliding latches 145A, 147A of the piston heads 134A, 134B to firmly secure the dome-shaped fastening members 161A, 161B to the piston heads 134A, 1334B. Because the membrane 140 is attached to the dome-shaped fastening members 161A, 161B, movement of the dome-shaped fastening members 161A, 161B into and out of the base 156 (e.g., due to reciprocating motion of the pistons 133A, 133B) causes the flexible membrane 140 to similarly be moved into and out of the recessed regions 162A, 162B of the base 156. This movement allows fluid to be forced out of and drawn into the fluid pump chambers 138A, 138B, which are formed between the recessed regions 162A, 162B of the base 156 and the portions of the dome-shaped fastening members 161A, 161B and membrane 140 that overlie those recessed regions 162A, 162B.

Raised ridges 167 extend from the substantially planar surface of the base 156 towards and into contact with the inner surface of the flexible membrane 140 when the cassette 112 is compressed between the door 108 and the cassette interface 110 of the PD machine 102 to form a series of fluid passageways 158 and to form the multiple, depressible dome regions 146, which are widened portions (e.g., substantially circular widened portions) of the fluid pathways 158, as shown in FIG. 6. The fluid passageways 158 fluidly connect the fluid line connectors 160 of the cassette 112, which act as inlet/outlet ports of the cassette 112, to the fluid pump chambers 138A, 138B. As noted above, the various inflatable members 142 of the PD machine 102 act on the cassette 112 during use. The dialysate flows to and from the pump chambers 138A, 138B through the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysate along the region of the pathway 158 associated with that dome region 146. Thus, the flow of the dialysate through the cassette 112 can be controlled through the selective depression of the depressible dome regions 146 by selectively inflating the inflatable members 142 of the PD machine 102.

The fluid line connectors 160 are positioned along the bottom edge of the cassette 112. As noted above, the fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysate bag lines 126, the heater bag line 128, the patient line 130, and the drain line 132. One end of the fitting can be inserted into and bonded to its respective line and the other end can be inserted into and bonded to its associated connector 160. By permitting the dialysate bag lines 126, the heater bag line 128, the patient line 130, and the drain line 132 to be connected to the cassette 112, as depicted in FIGS. 1 & 2, the connectors 160 allow dialysate to flow into and out of the cassette 112 during use. As the pistons 133A, 133B are reciprocated, the inflatable members 142 can be selectively inflated to allow fluid to flow from any of the lines 126, 128, 130, and 132 to any of ports 185A, 185B, 187A, and 187B of the pump chambers 138A, 138B or to allow fluid to flow from any of ports 185A, 185B, 187A, and 187B of the pump chambers 138A, 138B to any of the lines 126, 128, 130, and 132.

The rigidity of the base 156 helps to hold the cassette 112 in place within the cassette compartment 114 of the PD machine 102 and to prevent the base 156 from flexing and deforming in response to forces applied to the projections 154A, 154B by the dome-shaped fastening members 161A, 161B and in response to forces applied to the planar surface of the base 156 by the inflatable members 142. The dome-shaped fastening members 161A, 161B are also sufficiently rigid that they do not deform as a result of usual pressures that occur in the pump chambers 138A, 138B during the fluid pumping process. Thus, the deformation or bulging of the annular portions 149A, 149B of the membrane 140 can be assumed to be the only factor other than the movement of the pistons 133A, 133B that affects the volume of the pump chambers 138A, 138B during the pumping process.

The base 156 and the dome-shaped fastening members 161A, 161B of the cassette 112 can be formed of any of various relatively rigid materials. In some embodiments, these components of the cassette 112 are formed of one or more polymers, such as polypropylene, polyvinyl chloride, polycarbonate, polysulfone, and other medical grade plastic materials. In some embodiments, these components can be formed of one or more metals or alloys, such as stainless steel. These components can alternatively be formed of various different combinations of the above-noted polymers and/or metals/alloys. These components of the cassette 112 can be formed using any of various different techniques, including machining, molding, and casting techniques.

As noted above, the membrane 140 is attached to the periphery of the base 156 and to the annular flanges 164A, 164B of the dome-shaped fastening members 161A, 161B. The portions of the membrane 140 overlying the remaining portions of the base 156 are typically not attached to the base 156. Rather, these portions of the membrane 140 sit loosely atop the raised ridges 165A, 165B, and 167 extending from the planar surface of the base 156. Any of various attachment techniques, such as adhesive bonding and thermal bonding, can be used to attach the membrane 140 to the periphery of the base 156 and to the dome-shaped fastening members 161A, 161B. The thickness and material(s) of the membrane 140 are selected so that the membrane 140 has sufficient flexibility to flex toward the base 156 in response to the force applied to the membrane 140 by the inflatable members 142. In some embodiments, the membrane 140 is about 0.100 micron to about 0.150 micron in thickness. However, various other thicknesses may be sufficient depending on the type of material used to form the membrane 140. Any of various different materials that permit the membrane 140 to deflect in response to movement of the inflatable members 142 without tearing can be used to form the membrane 140. In some embodiments, the membrane 140 includes a three-layer laminate. In some embodiments, inner and outer layers of the laminate are formed of a compound that is made up of 60 percent Septon® 8004 thermoplastic rubber (i.e., hydrogenated styenic block copolymer) and 40 percent ethylene, and a middle layer is formed of a compound that is made up of 25 percent Tuftec® H1062 (SEBS: hydrogenated styrenic thermoplastic elastomer), 40 percent Engage® 8003 polyolefin elastomer (ethylene octane copolymer), and 35 percent Septon® 8004 thermoplastic rubber (i.e., hydrogenated styrenic block copolymer). The membrane 140 can alternatively include more or fewer layers and/or can be formed of different materials.

Figure 8:
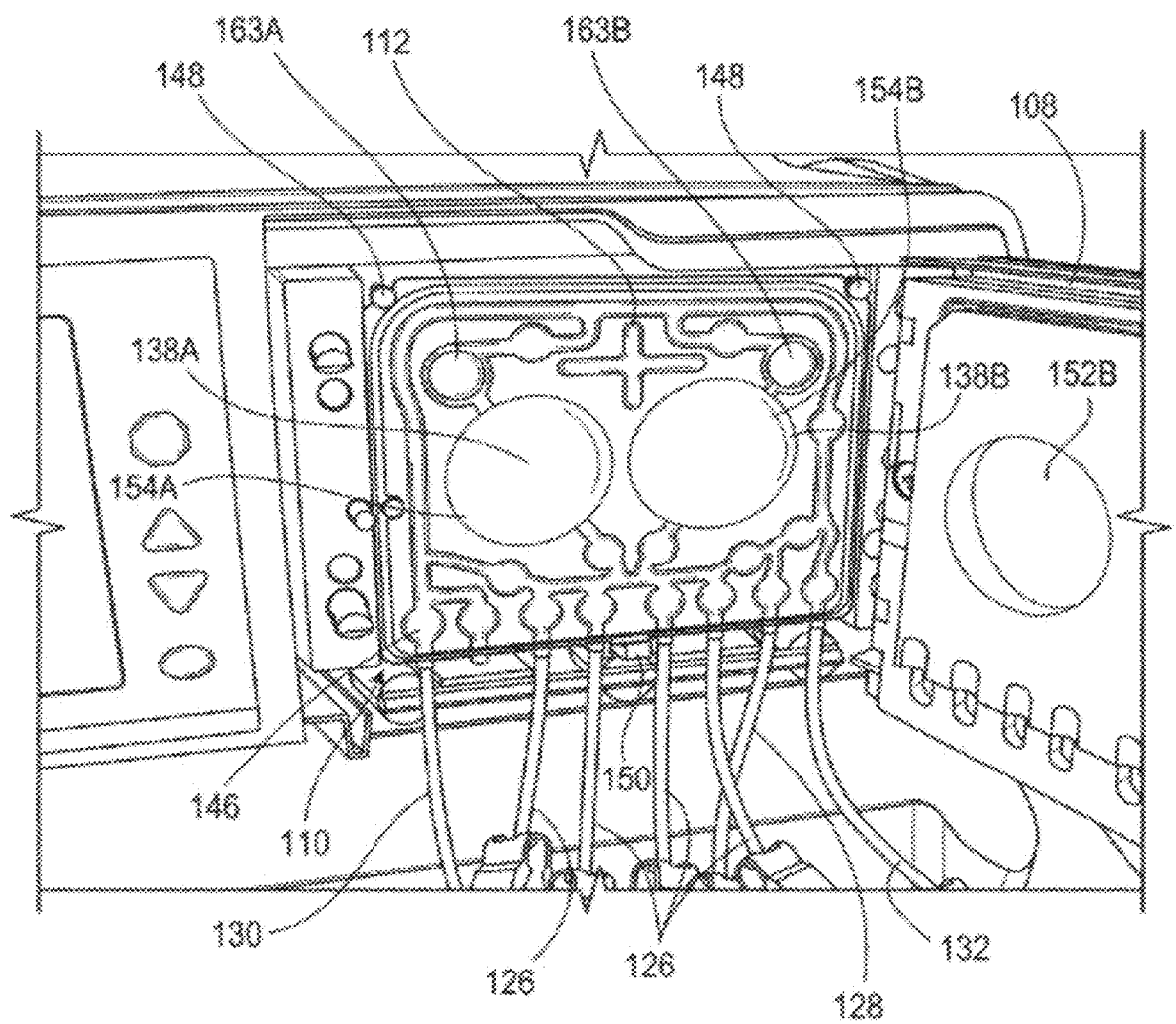
FIG. 8 illustrates the PD cassette seated against the cassette interface, in accordance with some embodiments.

FIG. 8 illustrates the PD cassette 112 seated against the cassette interface 110, in accordance with some embodiments. As depicted in FIG. 8, before starting a PD treatment, the door 108 of the PD machine 102 is opened to expose the cassette interface 110, and the cassette 112 is positioned with the dome-shaped fastening members 161A, 161B aligned with the pistons 133A, 133B of the PD machine 102, the pressure sensing chambers 163A, 163B aligned with the pressure sensors 151A, 151B of the PD machine 102, the depressible dome regions 146 aligned with the inflatable members 142 of the PD machine 102, and the membrane 140 adjacent to the cassette interface 110. In order to ensure that the cassette 112 is properly positioned on the cassette interface 110, the cassette 112 is positioned between the locating pins 148 and the spring loaded latch 150 extending from the cassette interface 110. The asymmetrically positioned connectors 160 of the cassette 112 act as a keying feature that reduces the likelihood that the cassette 112 will be installed with the membrane 140 and dome-shaped fastening members 161A, 161B facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward towards the door 108. The pistons 133A, 133B are typically retracted into the piston access ports 136A, 136B during installation of the cassette 112 to avoid interference between pistons 133A, 133B and the dome-shaped fastening members 161A, 161B and, therefore, increase the ease with which the cassette 112 can be positioned within the cassette compartment 114.

After positioning the cassette 112 as desired on the cassette interface 110, the door 108 is closed and the inflatable pad within the door 108 is inflated to compress the cassette 112 between the inflatable pad and the cassette interface 110. The compression of the cassette 112 holds the projections 154A, 154B of the cassette 112 in the recesses 152A, 152B of the door 108 and presses the membrane 140 tightly against the raised ridges 167 extending from the planar surface of the rigid base 156 to form the enclosed fluid pathways 158 and dome regions 146. The patient line 130 is then connected to a patient's abdomen via a catheter, and the drain line 132 is connected to a drain or drain receptacle. In addition, the heater bag line 128 is connected to the heater bag 124, and the dialysate bag lines 126 are connected to the dialysate bags 122. At this point, the pistons 133A, 133B can be coupled to the dome-shaped fastening members 161A, 161B of the cassette 112 to permit priming of the cassette 112 and one or more of the lines 126, 128, 130, and 132. Once these components have been primed, the PD treatment can be initiated.

FIGS. 9A-9G are cross-sectional views of the PD system 100 at various stages of setup, priming, and treatment, in accordance with some embodiments. The portion of the PD system 100 depicted in FIGS. 9A-9G focus on the interaction between the piston 133A of the PD machine 102 and the pump chamber 138A of the cassette 112 during the setup, priming, and treatment. The interaction between the other piston 133B and the other pump chamber 138B is similar to that shown in FIGS. 9A-9G and, therefore, will not be separately described herein to avoid repetition.

Figure 9A:
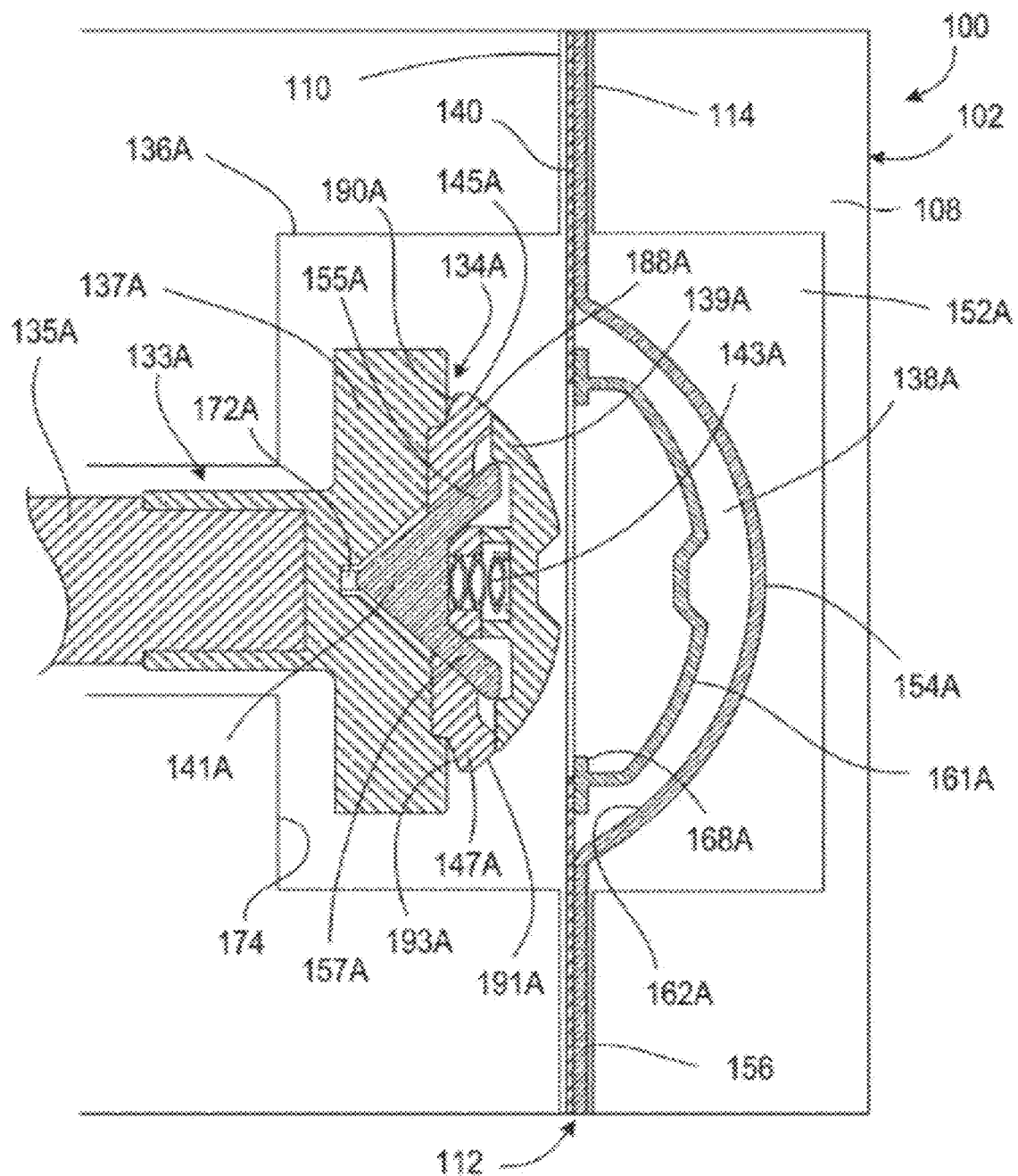
FIGS. 9A-9G are cross-sectional views of the PD system at various stages of setup, priming, and treatment, in accordance with some embodiments.

As depicted in FIG. 9A, the piston 133A is fully retracted into the piston access port 136A of the cassette interface 110. The cassette 112 is positioned in the cassette compartment 114 of the PD machine 102 and the inflatable pad in the door 108 of the PD machine 102 is inflated such that the cassette 112 is pressed tightly against the cassette interface 110 of the PD machine 102.

Figure 9B:
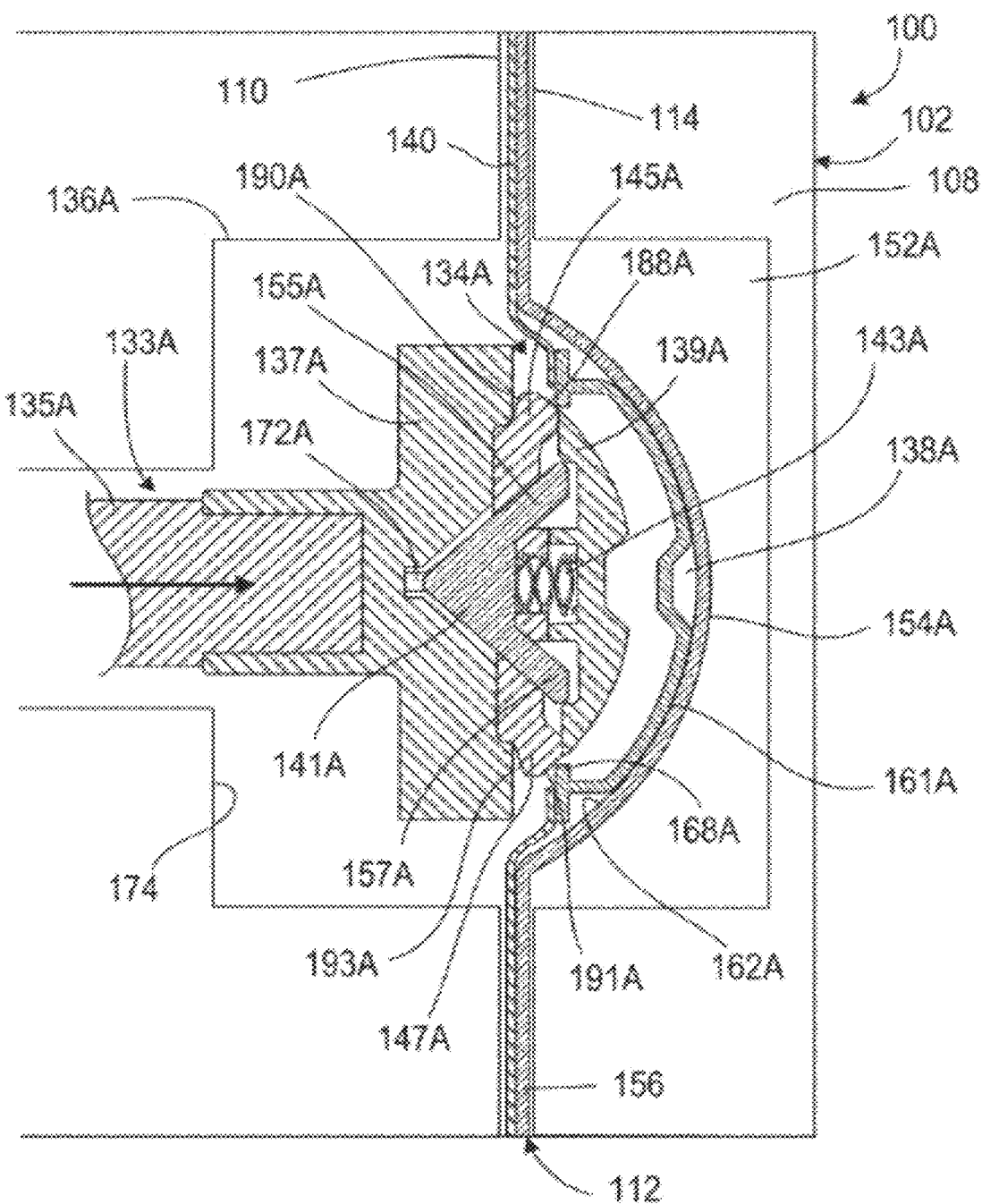

As depicted in FIG. 9B, with the cassette 112 properly installed within the cassette compartment 114 of the PD machine 102 and the appropriate line connections made, the piston 133A is advanced to initiate the process of mechanically connecting the piston head 134A of the PD machine 102 to the dome-shaped fastening member 161A of the cassette 112. As the piston 133A is advanced, a front angled surface 188A of a sliding latch 145A and a front angled surface 191A of a sliding latch 147A contact a rear surface of the annular projection 168A, which extends radially inward from the dome-shaped fastening member 161A. The rear surface of the annular projection 168A is approximately perpendicular to the longitudinal axis of the piston 133A.

As the piston 133A continues to advance, the dome-shaped fastening member 161A contacts the inner surface of the portion of the rigid base 156 that forms the recessed region 162A. The rigid base 156 prevents further forward movement of the dome-shaped fastening member 161A. The membrane 140, which is attached to the peripheral flange 164A of the dome-shaped fastening member 161A, also stretches and moves into the recessed region 162A due to the advancing piston 133A. Due to the angled geometries of the front angled surfaces 188A, 191A of the sliding latches 145A, 147A and the resistance provided by the rigid base 156 to the forward motion of the dome-shaped fastening member 161A, the sliding latches 145A, 147A are caused to move radially inward (e.g., toward the longitudinal axis of the piston 133A) as the piston head 134A continues to be advanced relative to the dome-shaped fastening member 161A. More specifically, the forward motion of the sliding latches 145A, 147A is converted into a combined forward and radially inward motion due to the sliding motion of the front angled surfaces 188A, 191A of the sliding latches 145A, 147A against the rear surface of the annular projection 168A of the dome-shaped fastening member 161A. The radial inward movement of each of the sliding latches 145A, 147A in turn causes a forward movement of a latch lock 141A of the piston head 134A due to the mated geometries of the outer surfaces of legs 155A, 157A of the latch lock 141A and the surfaces of the sliding latches 145A, 147A that are positioned adjacent to and brought into contact with those outer surfaces of the legs 155A, 157A. This forward movement of the latch lock 141A is resisted by a spring 143A disposed in a recessed portion of the piston head 134A.

Figure 9C:
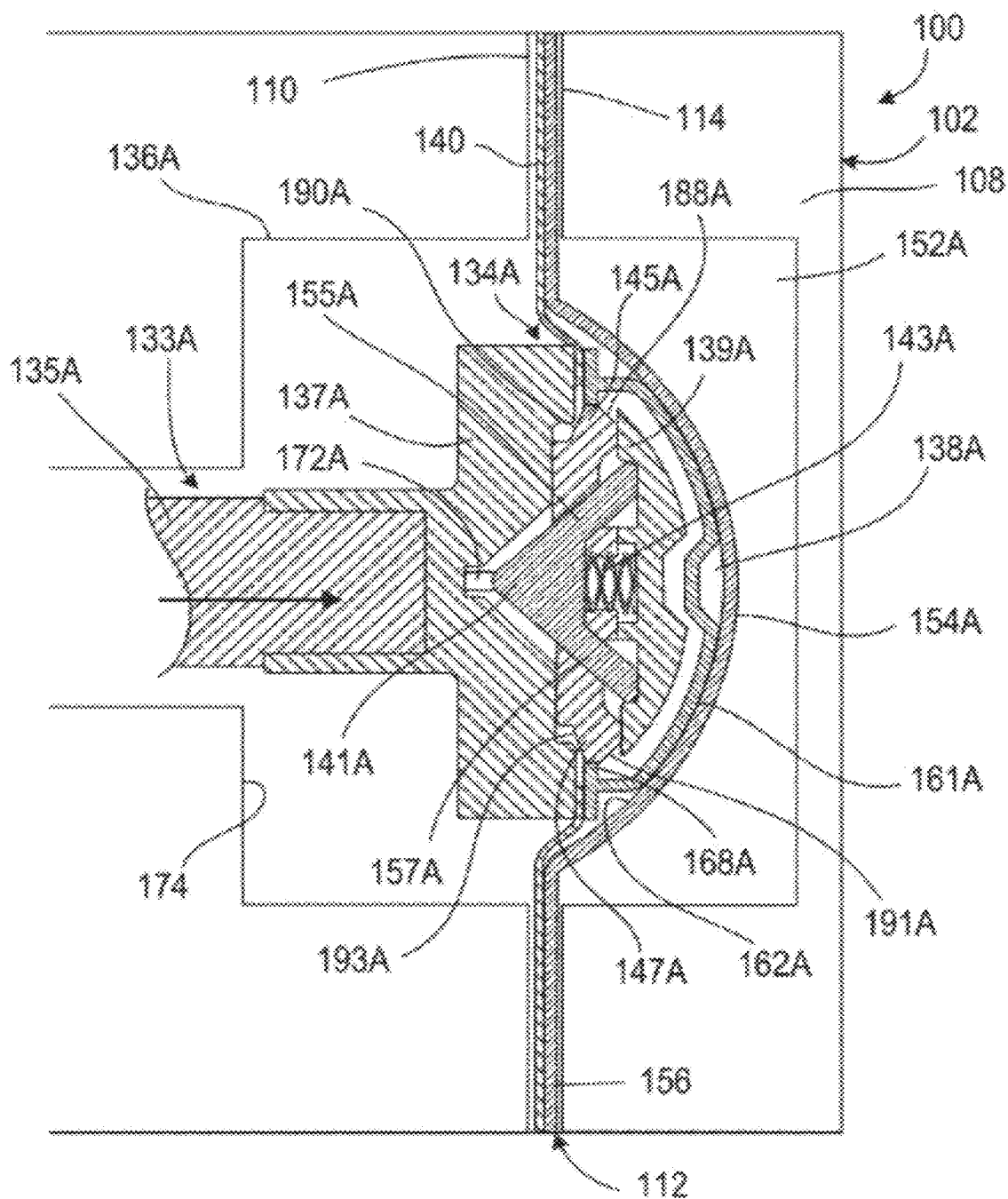

As depicted in FIG. 9C, the piston head 134A is located at a point during the connection process at which the sliding latches 145A, 147A have been deflected radially inward a sufficient distance to allow the sliding latches 145A, 147A to pass beyond the annular projection 168A that extends radially inward from the dome-shaped fastening member 161A. In this position, outer peripheral surfaces of the sliding latches 145A, 147A, which are substantially parallel to the longitudinal axis of the piston 133A, contact and slide along an inner surface of the annular projection 168A of the dome-shaped fastening member 161A, which is also substantially parallel to the longitudinal axis of the piston 133A. The spring 143A is further compressed due to the deflected positions of the sliding latches 145A, 147A.

Figure 9D:
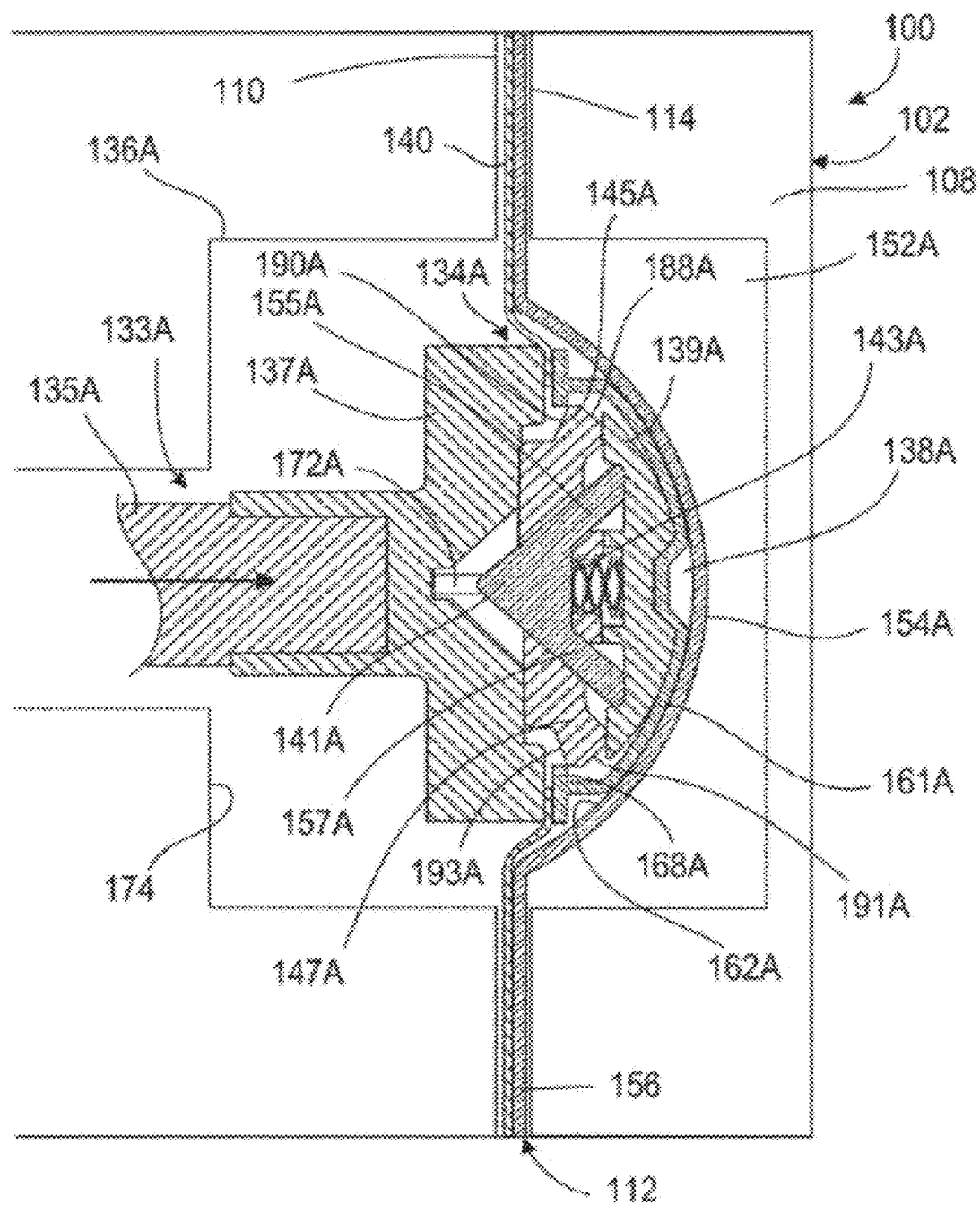

As depicted in FIG. 9D, as the sliding latches 145A, 147A pass beyond the annular projection 168A, the spring 143A is allowed to expand. The expansion of the spring 143A causes the latch lock 141A to move rearward. As a result, the outer surfaces of the legs 155A, 157A of the latch lock 141A contact the correspondingly angled adjacent surfaces of the sliding latches 145A, 147A, thereby causing the sliding latches 145A, 147A to move radially outward underneath the annular projection 168A of the dome-shaped fastening member 161A. Rear angled surfaces 190A, 193A of the sliding latches 145A, 147A ride along the front surface of the annular projection 168A of the dome-shaped fastening member 161A, which is slightly angled toward the rear of the dome-shaped fastening member 161A, as the sliding latches 145A, 147A move radially outward. The sliding latches 145A, 147A become wedged beneath the annular projection 168A as the sliding latches 145A, 147A move radially outward.

Figure 9E:
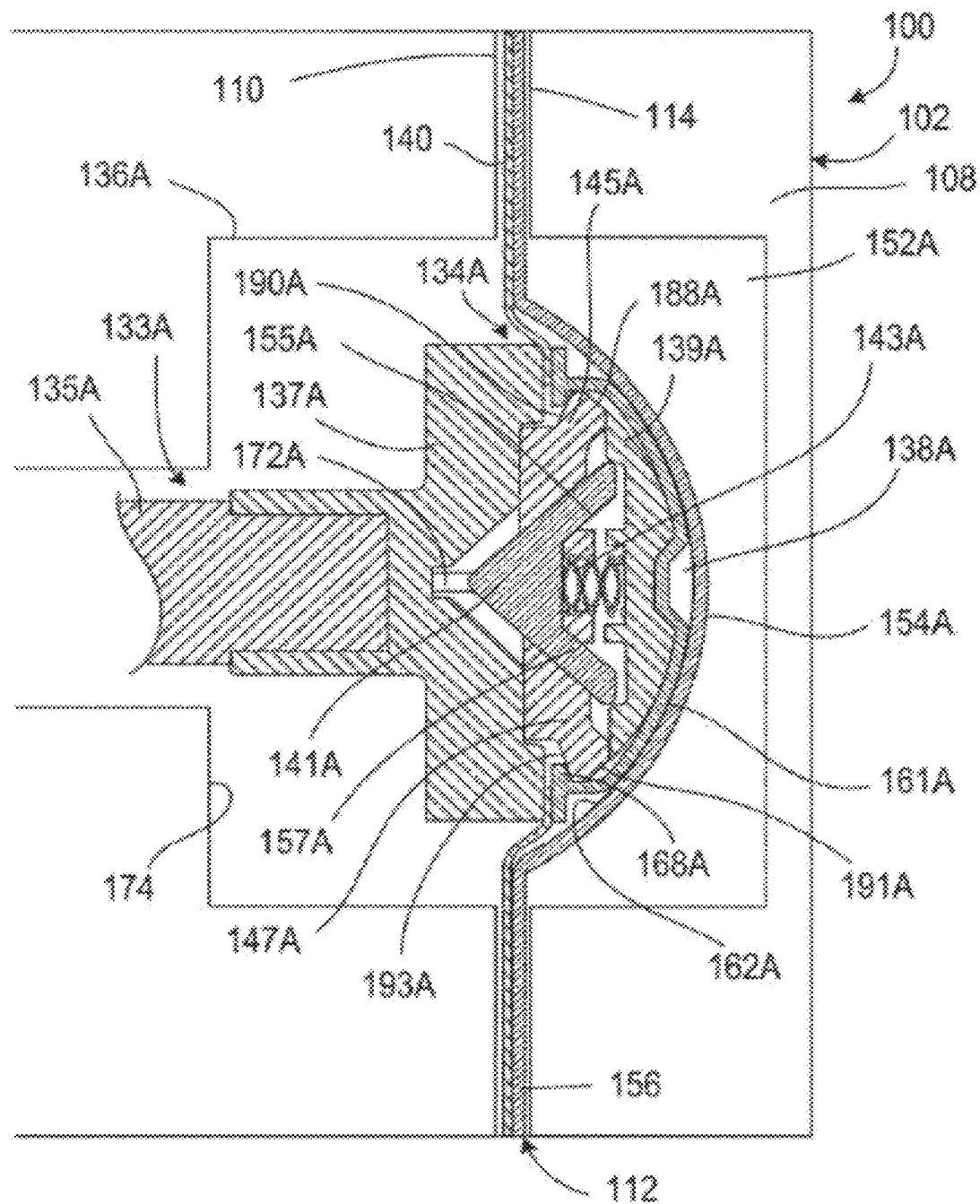

As depicted in FIG. 9E, the piston head 134A and the dome-shaped fastening member 161A are mechanically engaged through a mechanism in which the sliding latches 145A, 147A have moved to maximum outwardly displaced positions within the dome-shaped fastening member 161A on an interior side of the annular projection 168A. In this configuration, the annular projection 168A of the dome-shaped fastening member 161A is effectively pinched between a rear member 137A of the piston head 134A and rear angled surfaces 190A, 193A of the sliding latches 145A, 147A, resulting in a secure mechanical connection between the piston head 134A and the dome-shaped fastening member 161A. As a result of the mechanical engagement of the piston head 134A to the dome-shaped fastening member 161A, the amount of slippage of the piston head 134A relative to the dome-shaped fastening member 161A can be reduced (e.g., minimized) and thus precise pumping can be achieved.

After mechanically coupling the piston head 134A of the PD machine 102 to the dome-shaped fastening member 161A of the cassette 112, a priming procedure is carried out to remove air from the cassette 112 and from the various lines 126, 128, 130, and/or 132 connected to the cassette 112. In order to prime the cassette 112 and the lines 126, 128, 130, 132, the piston 133A and inflatable members 142 are typically operated to pump dialysate from the heater bag 124 to the drain and from each of the dialysate bags 122 to the drain. Dialysate is also passed (e.g., by gravity) from the heater bag 124 to the patient line 130 to force any air trapped in the patient line out of a hydrophobic filter positioned at the distal end of the patient line 130.

Figure 9F:
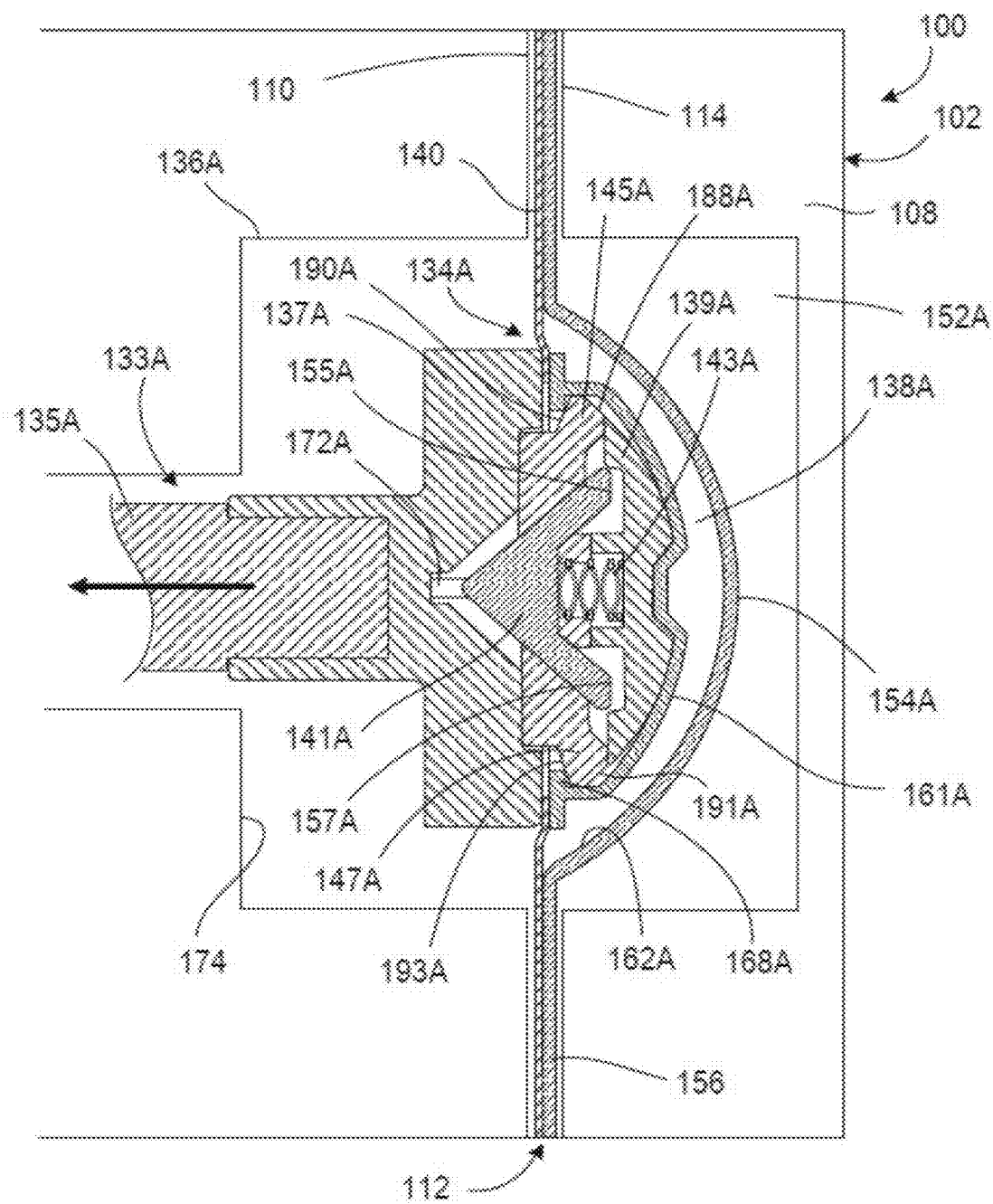

As depicted in FIG. 9F, after the priming procedure is complete, the patient line 130 is connected to the patient and the PD machine 102 is operated to drain any spent dialysate that was left in the patient's peritoneal cavity from a previous treatment. To drain the spent dialysate from the patient's peritoneal cavity, the inflatable members 142 of the PD machine 102 are configured to create an open fluid flow path between the patient line 130 and the port 187A (shown in FIG. 4) fluidly coupled to the pump chamber 138A, and the piston 133A is retracted to draw spent dialysate from the peritoneal cavity of the patient into the pump chamber 138A via the patient line 130. Because the piston head 134A is mechanically connected to the dome-shaped fastening member 161A and the dome-shaped fastening member 161A is attached to the membrane 140 of the cassette 112, the retraction of the piston 133A causes the dome-shaped fastening member 161A and the portion of the membrane 140 attached to the dome-shaped fastening member 161A to move rearward, away from the rigid base 156. As a result, the volume of the pump chamber 138A is increased reducing the pressure of fluid contained therein, and spent dialysate is drawn into the pump chamber 138A from the peritoneal cavity of the patient due to the pressure differential across the distal ends of the patient line 130. The spent dialysate travels from the patient line 130 through the pressure sensing chamber 163A of the cassette 112 and then enters the pump chamber 138A via the port 187A. The pressure sensor 151A monitors the fluid pressure in the pressure sensing chamber 163A, which is approximately equal to the fluid pressure in the pump chamber 138A, during this process.

Figure 9G:
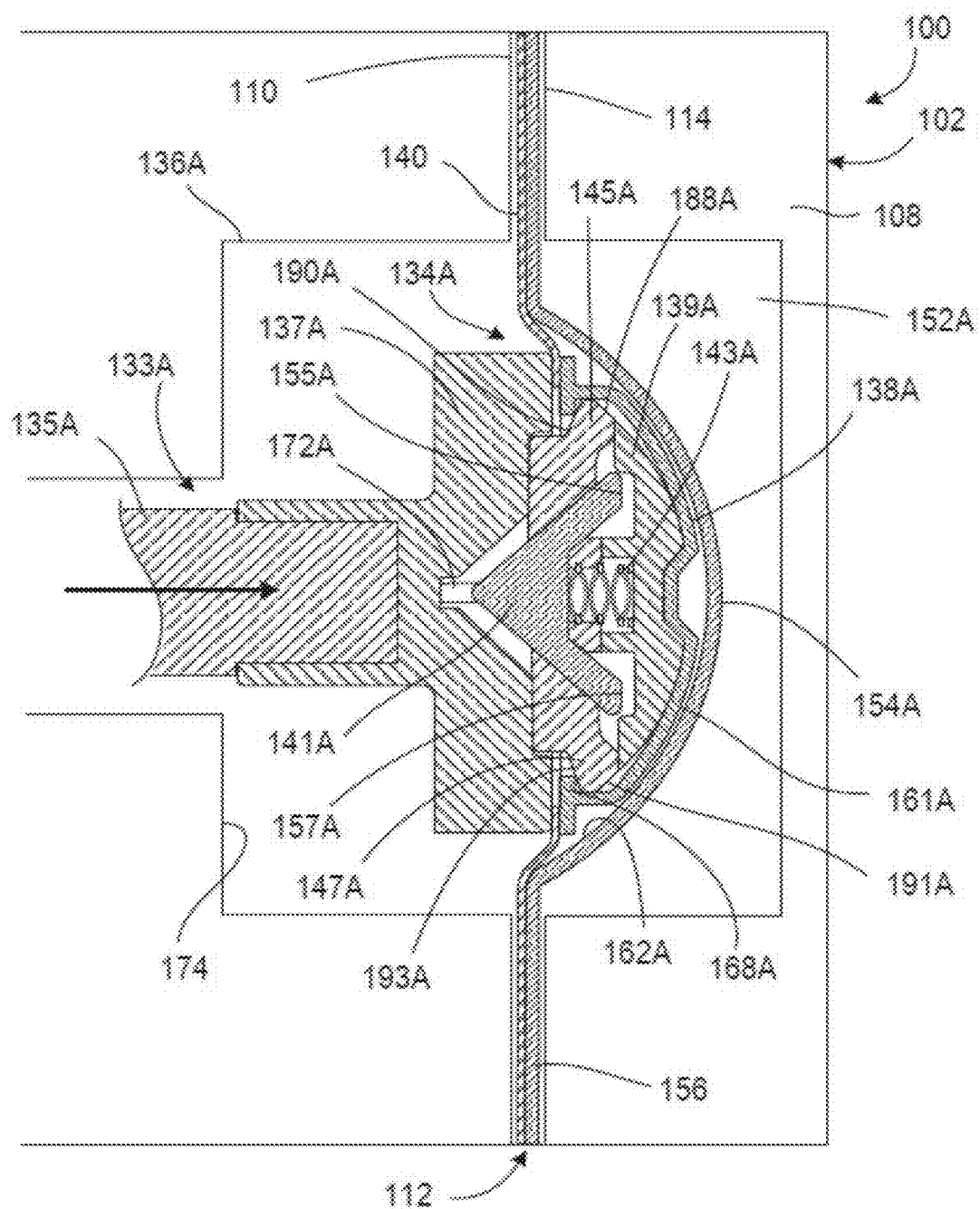

As depicted in FIG. 9G, after drawing the dialysate into the pump chamber 138A from the peritoneal cavity of the patient, the inflatable members 142 of the PD machine 102 are configured to create an open fluid flow path between the port 185A (shown in FIG. 4) fluidly coupled to the pump chamber 138A and the drain line 132, and the piston 133A is advanced to force dialysate out of the pump chamber 138A to the drain or drain receptacle. The piston 133A is typically advanced until the dome-shaped fastening member 161A contacts or nearly contacts the inner surface of the recessed region 162A of the base 156 so that substantially all of the dialysate is forced out of the fluid pump chamber 138A via the port 185A.

During the patient drain phase of the treatment, the pistons 133A, 133B are typically alternately operated such that the piston 133A is retracted to draw spent dialysate solution into the pump chamber 138A from the patient while the piston 133B is advanced to pump spent dialysate solution from the pump chamber 138B to the drain or drain receptacle, and vice versa.

To begin the patient fill phase, the inflatable members 142 are configured to create an open fluid flow path between the pump chamber 138A and the heater bag line 128, and then the piston 133A is retracted, as shown in FIG. 9F, to draw warm dialysate from the heater bag 124 to the pump chamber 138A. The warm dialysate travels from the heater bag 124 through the heater bag line 128 and into the pump chamber via the port 185A.

The warm dialysate is then delivered to the peritoneal cavity of the patient via the patient line 130 by configuring the inflatable members 142 to create an open fluid flow path between the pump chamber 138A and the patient line 130, and then the piston 133A is advanced, as shown in FIG. 9G, to pump warm dialysate to the patient. The warm dialysate exits the pump chamber 138A via the port 187A and travels through the pressure sensing chamber 163A to the patient line 130 before reaching the peritoneal cavity of the patient. The pressure sensor 151A monitors the fluid pressure in the pressure sensing chamber 163A, which is approximately equal to the fluid pressure in the pump chamber 138A, during this process.

During the patient fill phase of the treatment, the pistons 133A, 133B are typically alternately operated such that the piston 133A is retracted to draw warm dialysate into the pump chamber 138A from the heater bag 124 while the piston 133B is advanced to pump warm dialysate from the pump chamber 138B to the patient and vice versa. When the desired volume of dialysate has been pumped to the patient, the machine 102 transitions from the patient fill phase to a dwell phase. During the dwell phase, the dialysate is allowed to sit within the peritoneal cavity of the patient for a long period of time.

During the dwell phase (e.g., a period of time referred to as the dwell period), toxins cross the peritoneum of the patient into the dialysate from the patient's blood. As the dialysate dwells within the patient, the PD machine 102 prepares fresh dialysate for delivery to the patient in a subsequent cycle. In particular, the PD machine 102 pumps fresh dialysate from one of the four full dialysate bags 122 into the heater bag 124 for heating. To do this, the pump of the PD machine 102 is activated to cause the pistons 133A, 133B to reciprocate and certain inflatable members 142 of the PD machine 102 are inflated to cause the dialysate to be drawn into the fluid pump chambers 138A, 138B of the cassette 112 from the selected dialysate bag 122 via its associated line 126. The dialysate is then pumped from the fluid pump chambers 138A, 138B to the heater bag 124 via the heater bag line 128.

After the dialysate has dwelled in the patient for the desired period of time, the spent dialysate is pumped from the patient to the drain line 132 in the manner described above. The heated dialysate is then pumped from the heater bag 124 to the patient where it dwells for a desired period of time. These steps are repeated with the dialysate from two of the three remaining dialysate bags 122. The dialysate from the last dialysate bag 122 is typically delivered to the patient and left in the patient until the subsequent PD treatment.

After completion of the PD treatment, the pistons 133A, 133B are retracted in a manner to disconnect the piston heads 134A, 134B from the dome-shaped fastening members 161A, 161B of the cassette. The door 108 of the PD machine 102 is then opened and the cassette 112 is removed from the cassette compartment 114 and discarded.

Figure 10:
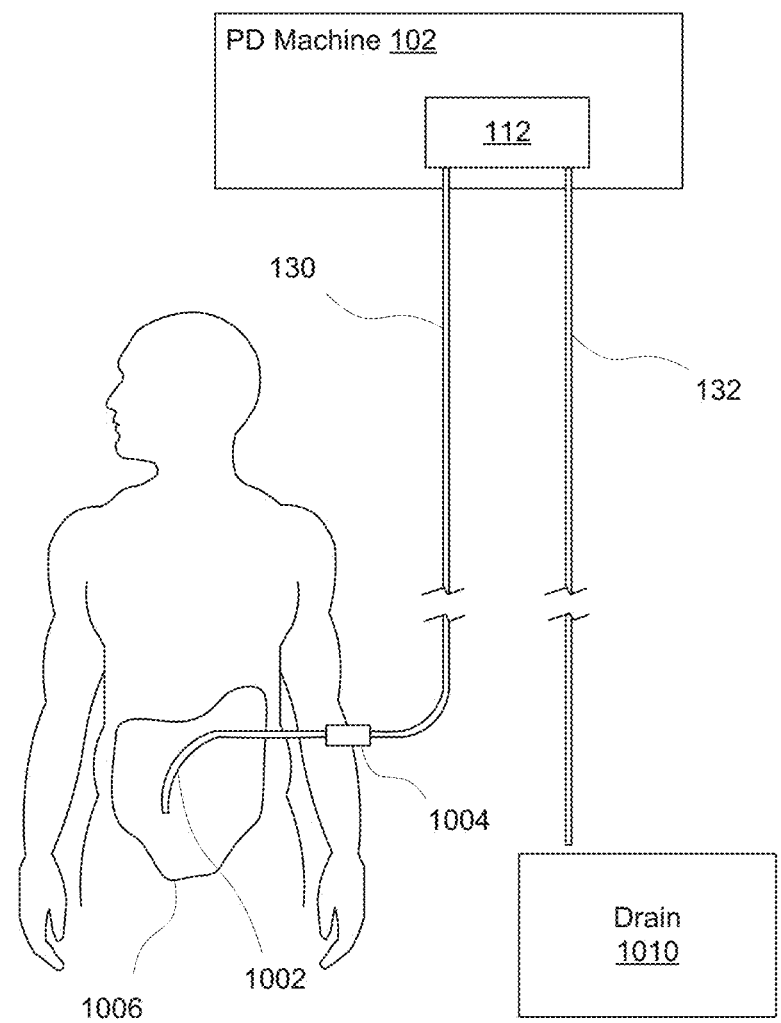
FIG. 10 illustrates a path between the patient and the PD machine when the patient is receiving a PD treatment, in accordance with some embodiments.

FIG. 10 illustrates a path between the patient and the PD machine 102 when the patient is receiving a PD treatment, in accordance with some embodiments. As depicted in FIG. 10, a proximal end of the patient line 130 is connected to the cassette 112 that is installed in the PD machine 102. A distal end of the patient line 130 is connected to the patient's abdomen 1006 via a catheter 1002. The catheter 1002 is connected to the patient line via a port 1004. In some embodiments, the patient line 130 can be a hollow tube formed from distensible and/or flexible material that is at least partially distended by operating pressures in the PD machine 102. In other words, fluid pressure causes the outer walls of the hollow tube to expand radially, thereby enabling the fluid to flow through the center of the tube. For example, in some embodiments, the patient line 130 can be made of an elastomeric material such as a polymer that expands in response to positive operating pressures in the fluid caused by the pumping action of the PD machine 102. The patient line 130, the port 1004, and the catheter 1002 are sometimes referred to as the patient line-catheter conduit, or simply conduit.

It will be appreciated that, during use, at least one of the pump chambers 138A, 138B and pressure sensing chambers 163A, 163B of the cassette 112 are fluidly coupled to the proximal end of the patient line 130 in order to induce fluid (e.g., dialysate solution) to flow through the patient line 130 in response to movement of the pistons 133A, 133B. The pressure sensors 151A, 151B can continuously monitor the fluid pressure in the corresponding pressure sensing chambers 163A, 163B. The signal generated by the pressure sensors 151A, 151B is indicative of the magnitude and direction of the fluid flow into or out of the pump chambers 138A, 138B and, due to a particular configuration of the inflatable members 142, can be indicative of the fluid flow through the patient line 130, drain line 132, dialysate bag lines 126, or heater bag line 128 (connected to a heater bag 124).

As depicted in FIG. 10, a proximal end of the drain line 132 is connected to the cassette 112, and a distal end of the drain line 132 is connected to a drain 1010 or a drain receptacle such as a bag, tub, or other receptacle capable of holding fluid. In some embodiments, the drain line 132 can be a hollow tube formed from distensible and/or flexible material that is at least partially distended by operating pressures in the PD machine 102. In some embodiments, the drain line 132 can be made of an elastomeric material such as a polymer that expands in response to positive operating pressures in the fluid caused by the pumping action of the PD machine 102. It will be appreciated that the distal end of the drain line 132 can be open to the air in order to promote fluid discharge into the drain 1010. In some embodiments, the drain line 132 can include a one-way valve, such as a check valve, that prevents backflow of fluid from the drain 1010 to the cassette 112. The one-way valve can also prevent air in the drain line from being introduced into the cassette 112, which can decrease the reliability of readings of the pressure sensors 151A, 151B.

Figure 11A:
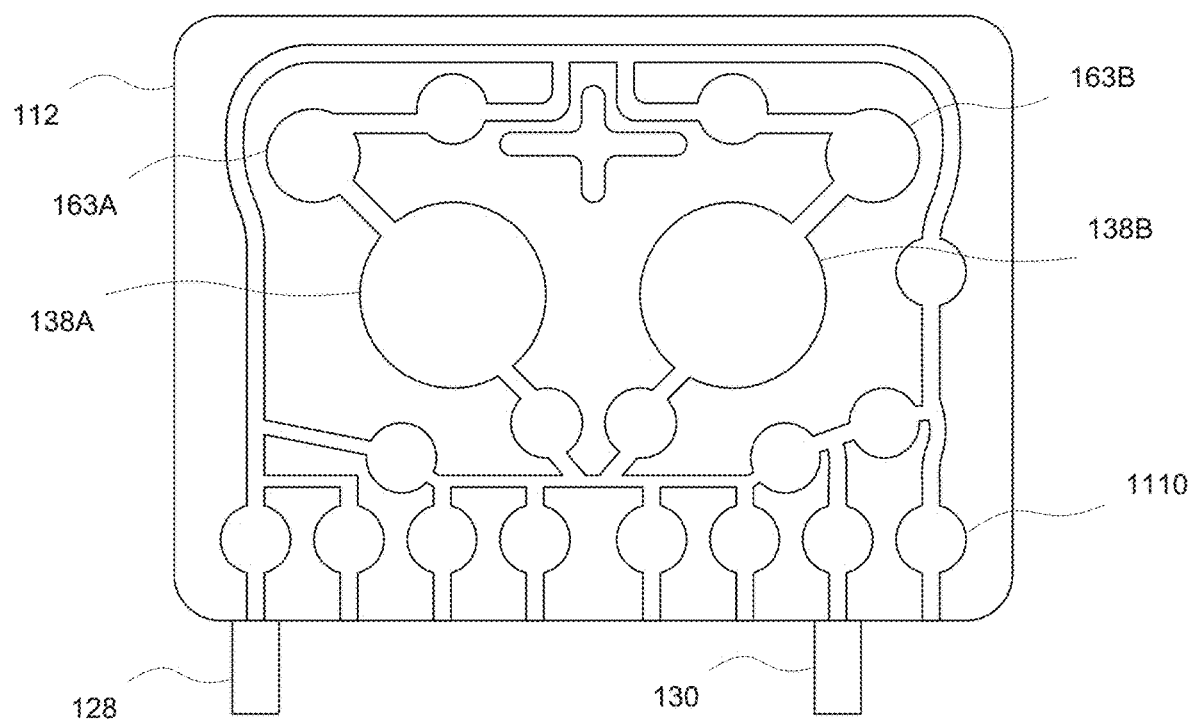
FIGS. 11A-11F illustrate a fluid flow path through the cassette from the heater bag line to the patient line, in accordance with some embodiments.

FIGS. 11A-11F illustrate a fluid flow path through the cassette 112 from the heater bag line 128 to the patient line 130, in accordance with some embodiments. As depicted in FIG. 11A, the cassette 112 includes pump chambers 138A, 138B, pressure sensing chambers 163A, 163B, and a plurality of valve chambers 1110. The valve chambers 1110 control the flow of fluid through the cavities of the cassette 112.

During conventional operation, the fluid (e.g., dialysate) is pumped from the heater bag line 128 to the patient line 130 using alternating flow paths through either the first pump chamber 138A or the second pump chamber 138B. The configuration of the valve chambers 1110 during each stroke of the pistons 133A, 133B determined whether a particular volume of fluid was pumped into the first pump chamber 138A or the second pump chamber 138B, and that particular volume of fluid was not pumped into the other pump chamber before being expelled into the patient line 130. While the pressure sensing chambers 163A, 163B and the pistons 133A, 133B could be used to measure or estimate a volume of fluid in the pump chambers 138A, 138B during operation to, e.g., detect issues such as possible line occlusions, leaks in the lines, a ruptured cassette 112, and so forth, the total amount of fluid passing through the cassette 112 is typically not accumulated based on these measurements.

In some embodiments, a fluid flow path through the cassette 112 can be modified in order to increase an accuracy of a measurement of a total fluid volume passing through the cassette 112 during operation of the PD cycler. A plurality of measurements for each particular volume of fluid can be measured in multiple different pump chambers of the cassette 112. For example, as shown in the cassette 112 of FIG. 11A, measurements of a fluid volume can be taken in the first pump chamber 138A and the second pump chamber 138B. The individual measurements can be compared and, in some embodiments, an estimate of the fluid volume for the particular volume of fluid can be calculated. In some embodiments, the estimate of the fluid volume is a mean of the individual measurements. In addition, in some embodiments, a range of the measurements can be calculated, and if the range is greater than a threshold value, then an alert can be set that can indicate a potential issue with the PD cycler. It will be appreciated that the volumes of the pump chambers 138A, 138B should be the same, although in practice, due to unit to unit variation in manufacture, the volumes may not be exactly the same. A fluid volume measurement of the fluid in the first pump chamber 138A should be the same as (or substantially similar to) a second fluid volume measurement in the second pump chamber 138B after that fluid has been pumped from the first pump chamber 138A to the second pump chamber 138B. If the first measurement differs significantly from the second measurement, then the difference could be an indication of an issue such as a faulty pressure sensor, a broken piston, a blockage or manufacturing defect in the cassette 112, a leak in the cassette 112, or the like.

Figure 11B:
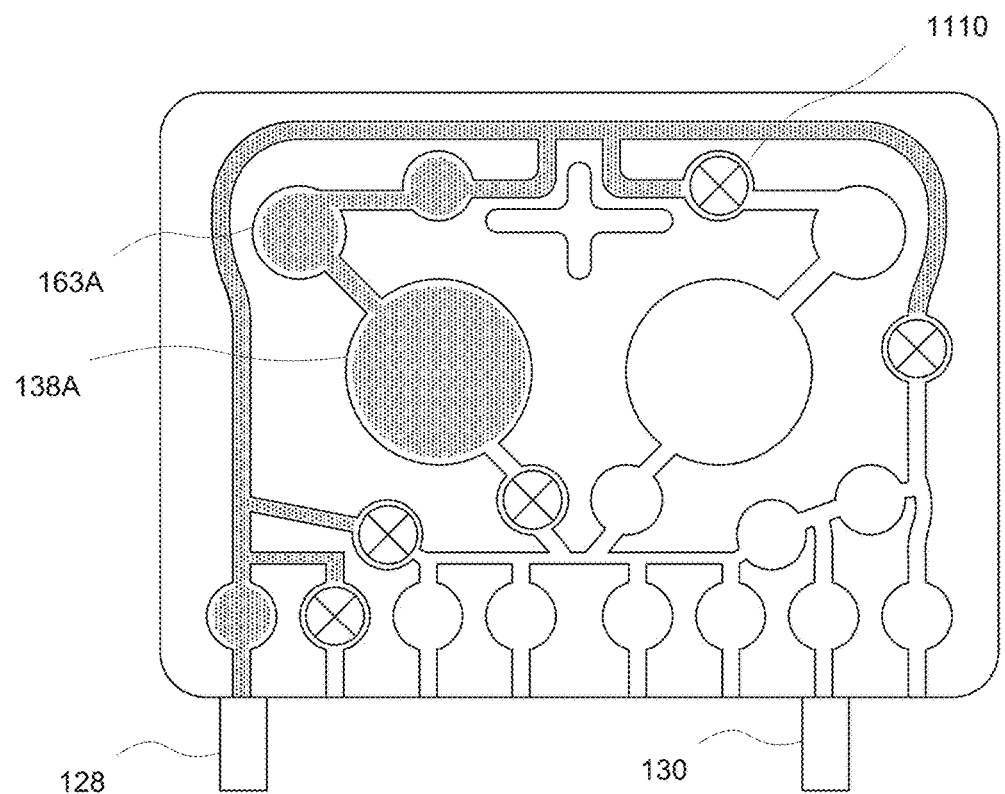

As depicted in FIG. 11B, during a first period of time, the PD cycler operates a first piston 133A, connected to the dome-shaped fastening member 161A, to draw fluid into a first pump chamber 138A. As the piston 133A retracts into the PD cycler, the pressure in the first pump chamber 138A drops (due to the increased volume of the first pump chamber 138A), thereby drawing fluid from the heater bag line 128 into the first pump chamber 138A (and all cavities and valve chambers 1110 in the fluid flow path therebetween). Fluid is shown as a filled pattern within the cavities, valve chambers 1110, the first pressure chamber 163A, or the first pump chambers 138A of the cassette 112. Valve chambers 1110 illustrated with an X enclosed within a circle indicates that the valve chamber 1110 is closed (e.g., fluid cannot pass through the valve chamber 1110) Valve chambers 1110 illustrated with a filled pattern therein indicates that the valve chamber 1110 is open (e.g., fluid can pass through the valve chamber 1110). Valve chambers 1110 shown as empty are in either a closed or an open state, depending on additional fluid paths formed in the cassette 112 during the first period of time consistent with other parallel operations. For example, it will be appreciated that the configurations of valve chambers 1110 shown in FIG. 11B could allow for fluid to be pumped out of the second pump chamber 138B in parallel with fluid being pumped into the first pump chamber 138A.

Figure 11C:
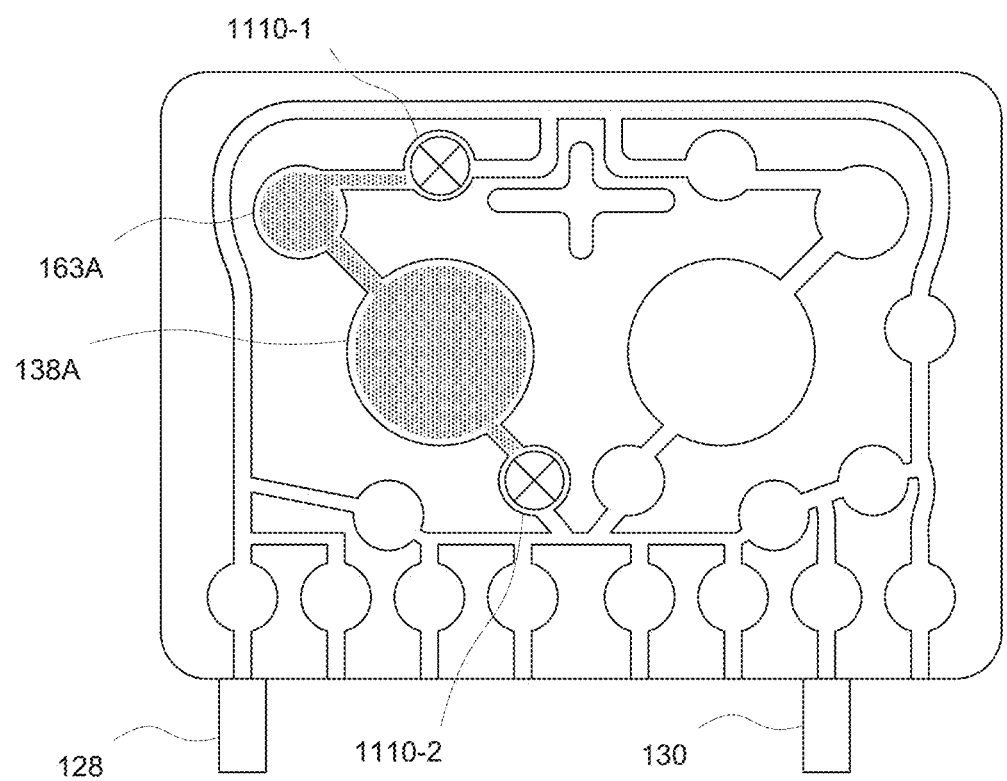

As depicted in FIG. 11C, during a second period of time, the PD cycler closes valve chambers 1110-1 and 1110-2 to trap a volume of fluid in the first pump chamber 138A and the first pressure chamber 163A, as well as the cavities connected thereto. The piston 133A extends from the PD cycler thereby reducing a volume in the first pump chamber 138A. Monitoring a pressure signal from a pressure transducer in contact with the first pressure chamber 163A, the controller 139 can determine when the location of the piston head 134A corresponds to the volume of fluid in the first pump chamber 138A based on a rise in pressure detected by the pressure transducer. In other words, due to the incompressible characteristic of the fluid, the pressure significantly rises due to operation of the piston 133A at a point when any air in the first pump chamber 138A has already been compressed and the piston 133A is primarily acting on the fluid. At this point, the volume of the fluid in the first pump chamber 138A is well-matched to the volume of the cassette 112 between the first valve chamber 1110-1 and the second valve chamber 1110-2, including the volume of the first pump chamber 138A and the first pressure chamber 163A, plus cavities connected thereto, and a measured location of the piston head 134A provides an accurate first fluid volume measurement.

Given unit-to-unit variation of different cassettes 112 (e.g., manufacturing tolerances, defects, etc.), the measurement taken by the control unit 139 is associated with a certain accuracy, which may be unknown. However, by taking independent measurements of the same data point, the accuracy of the measurement can be increased. Given that the nominal volume of the first pump chamber 138A is the same as the nominal volume of the second pump chamber 138B, and the nominal volume of the first pressure chamber 163A is the same as the nominal volume of the second pressure chamber 163B, a second independent measurement can be taken of the same volume of fluid by transferring the fluid from the first pump chamber 138A to the second pump chamber 138B and taking another independent measurement.

Figure 11D:
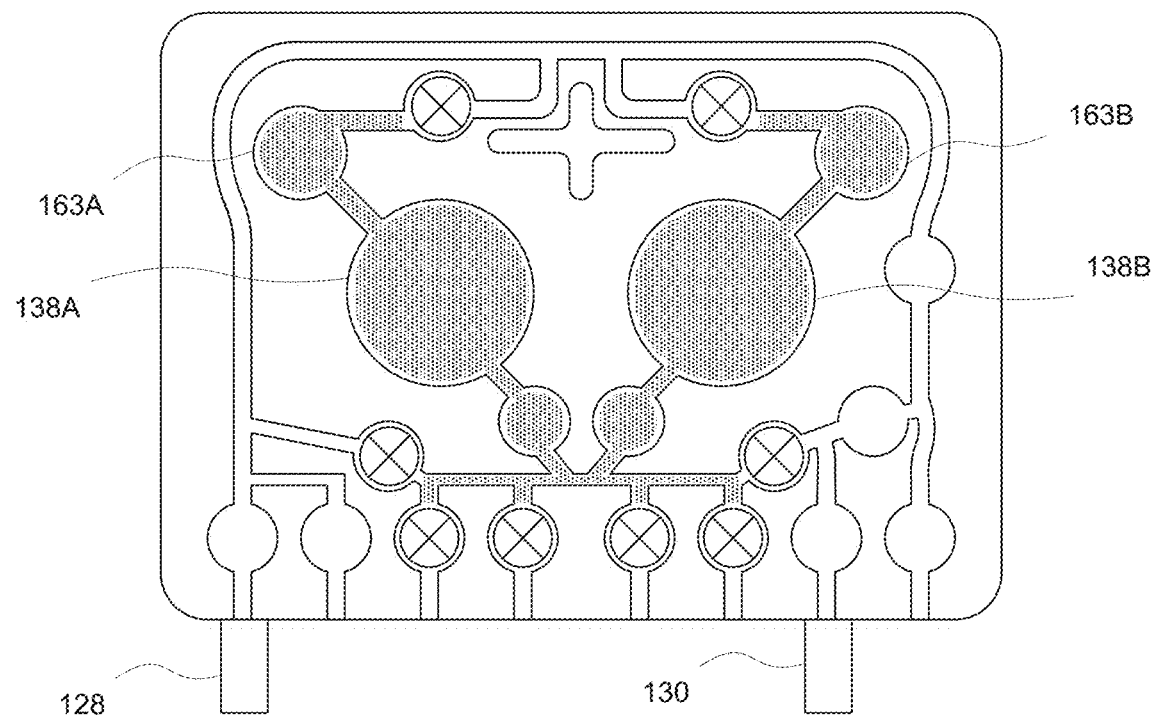

As depicted in FIG. 11D, during a third period of time, the PD cycler closes valve chambers to create a fluid flow path between the first pump chamber 138A and the second pump chamber 138B. Valve chamber 1110 are opened to facilitate the flow of fluid between the first pump chamber 138A and the second pump chamber 138B. Fluid is forced out of the first pump chamber 138A by the first piston 133A extending from the PD cycler and into the second pump chamber 138B by the second piston 133B retracting into the PD cycler.

Figure 11E:
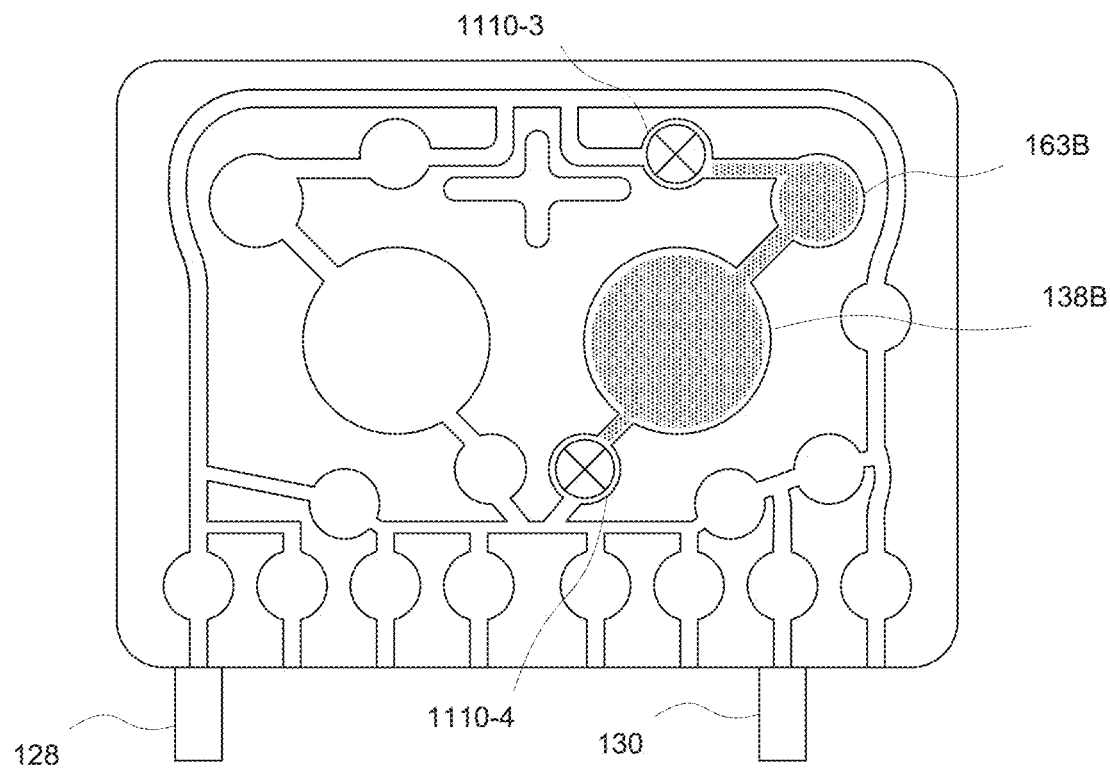

As depicted in FIG. 11E, during a fourth period of time, the PD cycler closes valve chambers 1110-3 and 1110-4 to trap the volume of fluid in the second pump chamber 138B and the first pressure chamber 163B, as well as the cavities connected thereto. The piston 133B extends from the PD cycler thereby reducing a volume in the second pump chamber 138B. Similar to the discussion above with respect to FIG. 11C, monitoring a pressure signal from a pressure transducer in contact with the second pressure chamber 163B, the controller 139 can determine when the location of the piston 133B is indicative of the volume of fluid in the second pump chamber 138B. In other words, given the measured location of the piston head 134B, a volume of the cassette 112 between the third valve chamber 1110-3 and the fourth valve chamber 1110-4, including the volume of the second pump chamber 138B and the second pressure chamber 163B, plus cavities connected thereto, can be estimated based on a rise in pressure due to the incompressible characteristic of the fluid as the volume of the cassette 112 between the third valve chamber 1110-3 and the fourth valve chamber 1110-4 is reduced due to operation of the piston 133B.

The second measurement provides a second estimate of what should be the same volume of fluid that passed through, and was measured in, the first pump chamber 138A. Consequently, the second measurement provides a second data point of the same property of the fluid. It will be appreciated that due to variations of the cassette 112, the volume of the first pump chamber 138A may not be equal to the volume of the second pump chamber 138B. Consequently, a better estimate of the actual volume of fluid can be estimated by performing a statistical analysis of the independent data points.

In one embodiments, the control unit 139 estimates the volume of fluid by calculating a mean (e.g., an average) of a plurality of independent measurements taken in different pump chambers 138 of the cassette 112. It will be appreciated that the PD cycler illustrated herein utilizes two pistons and two pump chambers. However, the description is not so limited and various embodiments of different PD cyclers could incorporate additional pump chambers/pistons to allow for more than two independent measurements. For example, the technique described above can be extended to a cassette with three or more pump chambers and a PD cycler with three or more pistons configured to operate as pumps. In such systems, three or more independent measurements can be combined (e.g., by taking a mean of all independent values) to estimate the fluid flow volume through the PD cycler.

Figure 11F:
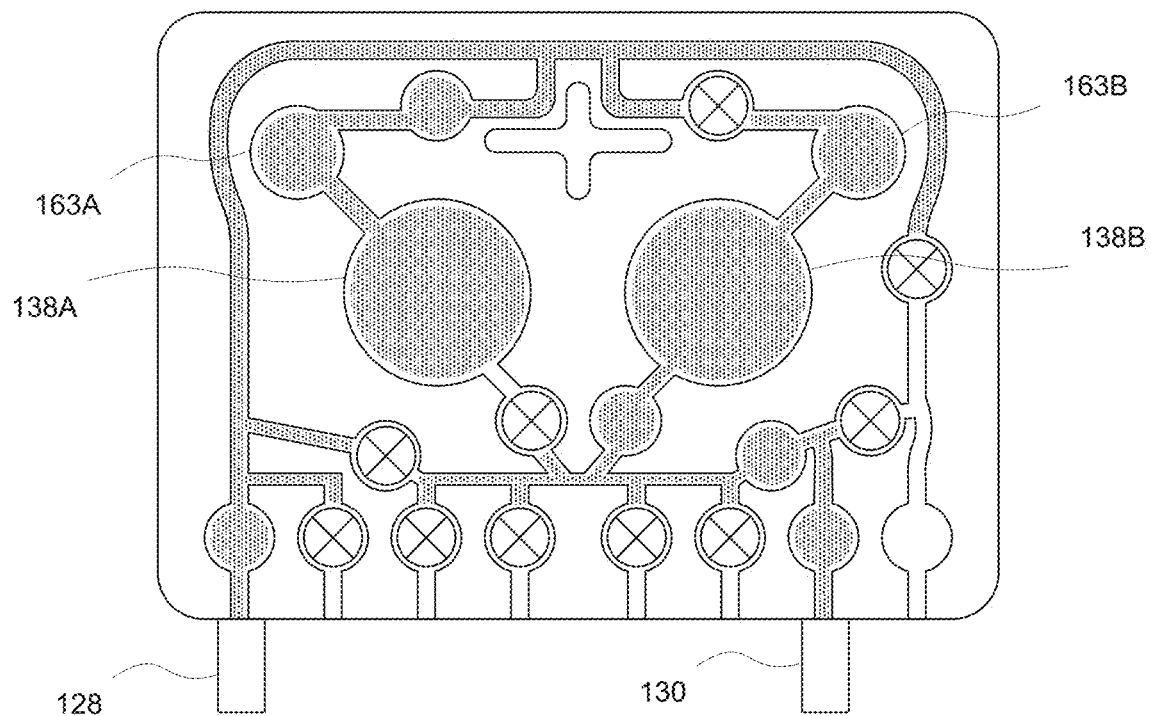

As depicted in FIG. 11F, during a fifth period of time, the fluid in the second pump chamber 138B is forced from the second pump chamber 138B into the patient line 130, via the configuration of valve chambers as illustrated. It will be appreciated that while the piston 133B is forcing the fluid from the second pump chamber 138B into the patient line 130, the other piston 133A can be drawing fluid from the heater bag line 128 into the first pump chamber 138A in order to take a first measurement of a second volume of fluid. Over a number of cycles as depicted in FIGS. 11B-11F, a total volume of fluid passing through the cassette 112 can be tracked by accumulating the estimates for each discrete volume of fluid passing through the plurality of pump chambers 138. This estimated total volume can then be utilized by the PD cycler to determine when a given dialysate bag (e.g., the heater bag 124) may be close to empty. In some embodiments, the control unit 139 can utilize the estimated total volume to start a refill cycle where dialysate is pumped from a second dialysate bag into the heater bag 124.

A reverse process can be used to monitor the flow of fluid into the heater bag line 128 from one of the other line connections to the cassette 112. More specifically, during a refill cycle, fluid from a second dialysate bag pumped to the heater bag 124 can be measured and the fluid volumes can be accumulated into the estimated total volume. For example, the incremental volume measurements for each pump cycle can be added to the estimated total volume to monitor the amount of dialysate in the heater bag 124 as fluid is added to the heater bag 124.

Figure 12:
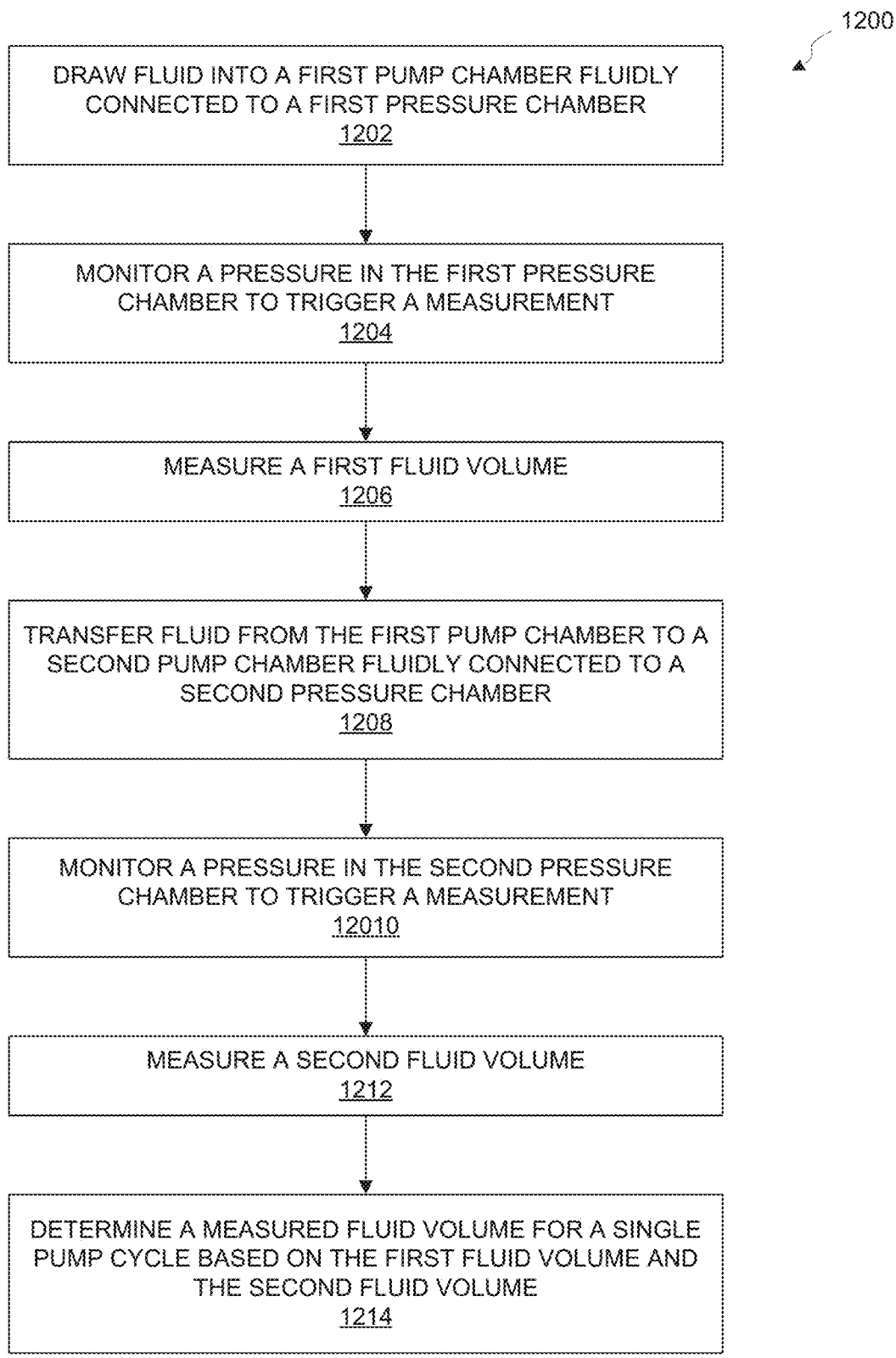
FIG. 12 is a flow diagram of a method for measuring fluid flow in a peritoneal dialysis machine, in accordance with some embodiments.

FIG. 12 is a flow diagram of a method 1200 for measuring fluid flow in a peritoneal dialysis machine, in accordance with some embodiments. It will be appreciated that the method 1200 is described as being performed by the PD system 100. More specifically, the various steps described below can be implemented by a processor, such as the control unit 139 of the PD machine 102, configured to execute a number of instructions. However, it will be appreciated that the method 1200 can be performed by any PD machine configured to drain fluid from a peritoneal cavity of a patient during a PD cycle. In various embodiments, the method 1200 can be implemented using hardware, software executed by a general purpose processor configured to control a specialized apparatus such as a PD machine, or a combination of hardware and software.

At step 1202, a fluid, such as dialysate, is drawn into a first pump chamber 138A fluidly connected to a first pressure chamber 163A. In some embodiments, a cassette 112 is loaded into a PD machine 102. A first piston 133A is engaged with a first pump chamber 138A. In an embodiment, a piston head 134A is engaged with a dome-shaped fastening member 161A that allows the piston 133A to change the volume of the first pump chamber 138A. Operation of the first piston 133A, retracting into the PD machine 102, increases the volume of the first pump chamber 138A and draws fluid from a connected heater bag line 128 through a fluid path in the cassette 112.

At step 1204, a pressure in the first pressure chamber 163A is monitored by a control unit 139. In an embodiment, after the first piston 133A is fully retracted such that fluid has been drawn into the first pump chamber 138A, a first set of valve chambers 1110 are closed to confine a portion of the fluid in a first portion of the cassette 112. The first portion of the cassette 112 includes the first pump chamber 138A fluidly connected to the first pressure chamber 163A. The piston 133A is extended from the PD machine 102 to reduce the volume of the first pump chamber 138A while the control unit 139 monitors a pressure signal from a pressure transducer configured to measure a fluid pressure in the first pressure chamber 163A. The first piston 133A is extended to reduce the volume of the first pump chamber 138A, thereby compressing the air and fluid trapped therein. As the air is compressed, the pressure signal can experience a slight rise due to the compressible nature of air. However, at a point where the air has been significantly compressed and an extended position of the first piston 133A has reduced a volume of the first pump chamber 138A such that the volume of fluid is substantially equal to the volume of the first portion of the cassette 112, the pressure signal will experience a significant change in slope and a rapid rise due to the incompressible nature of the fluid in comparison to the air. Consequently, this change in the pressure signal can be used to trigger a measurement of the first fluid volume trapped in the first portion of the cassette 112.

At step 1206, a first fluid volume is measured in the first portion of the cassette 112. The measurement can be triggered by the change in the pressure signal in step 1204. The control unit 139 takes a measurement of the first fluid volume, which is based on the current position of the piston 133A when the control unit 139 detects the change in the pressure signal. It will be appreciated that the position of the piston 133A indicates a volume of the first pump chamber 138A and the first portion of the cassette 112. In an embodiment, the position of the piston 133A is given, for example, by an optical encoder signal coupled to a lead screw that actuates the piston 133A. In other embodiments, the position can be sensed using other technically feasible techniques such as by counting stepper motor steps to infer a position of the stepper motor or using other feedback signals from other types of sensors.

At step 1208, the fluid is transferred from a first pump chamber 138A to a second pump chamber 138B fluidly connected to a second pressure chamber 163B. In some embodiments, the valve chambers 1110 are configured to create a fluid path in the cassette 112 that connects the first pump chamber 138A to the second pump chamber 138B. The first piston 133A is extended and the second piston 133B is retracted to move fluid from the first pump chamber 138A to the second pump chamber 138B.

At step 1210, a pressure in the second pressure chamber 163B is monitored by a control unit 139. Similar to step 1204 for the first pressure chamber 163A, after the second piston 133B is fully retracted such that the fluid has been drawn into the second pump chamber 138B, a second set of valve chambers 1110 are closed to confine the fluid in a second portion of the cassette 112. The second portion of the cassette 112 includes the second pump chamber 138B fluidly connected to the second pressure chamber 163B. The piston 133B is extended from the PD machine 102 to reduce the volume of the second pump chamber 138B while the control unit 139 monitors a pressure signal from a pressure transducer configured to measure a fluid pressure in the second pressure chamber 163B. The second piston 133B is extended to reduce the volume of the second pump chamber 138B, thereby compressing the air and fluid trapped therein. As the air is compressed, the pressure signal can experience a slight rise due to the compressible nature of air. However, at a point where the air has been significantly compressed and an extended position of the second piston 133B has reduced a volume of the second pump chamber 138B such that the volume of fluid is substantially equal to the volume of the second portion of the cassette 112, the pressure signal will experience a significant change in slope and a rapid rise due to the incompressible nature of the fluid in comparison to the air. Consequently, this change in the pressure signal can be used to trigger a measurement of the second fluid volume trapped in the second portion of the cassette 112.

At step 1212, a second fluid volume is measured in the second portion of the cassette 112. The measurement can be triggered by the change in the pressure signal in step 1210. The control unit 139 takes a measurement of the second fluid volume, which is based on the current position of the piston 133B when the control unit 139 detects the change in the pressure signal. It will be appreciated that the position of the piston 133B indicates a volume of the second pump chamber 138A and the second portion of the cassette 112. In an embodiment, the position of the piston 133B is given be an optical encoder signal coupled to a lead screw that actuates the piston 133B. In other embodiments, the position can be sensed using other technically feasible techniques.

At step 1214, a measured fluid volume for a single pump cycle is determined by the control unit 139 based on the first fluid volume and the second fluid volume. In an embodiment, an average of the measured fluid volumes in each portion of the cassette 112 is calculated as the measured fluid volume. In other embodiments, the minimum or maximum fluid volume can be selected as the measured fluid volume.

Although the method 1200 is based on a cassette 112 with two distinct pump chambers 138, in other embodiments, the method 1200 can be extended to cassettes 112 with three or more pump chambers by repeating steps 1208 through 1212 for each additional pump chamber and then determining the measured fluid volume based on all independent measurements for each of the three or more pump chambers.

It will be appreciated that the terms "less than" or "greater than," as used above, can encompass "less than or equal to" or "greater than or equal to," respectively, and that the decision of whether the comparison is inclusive or exclusive of the threshold value is merely a design choice unless otherwise clearly contradicted by the context.

Figure 13:
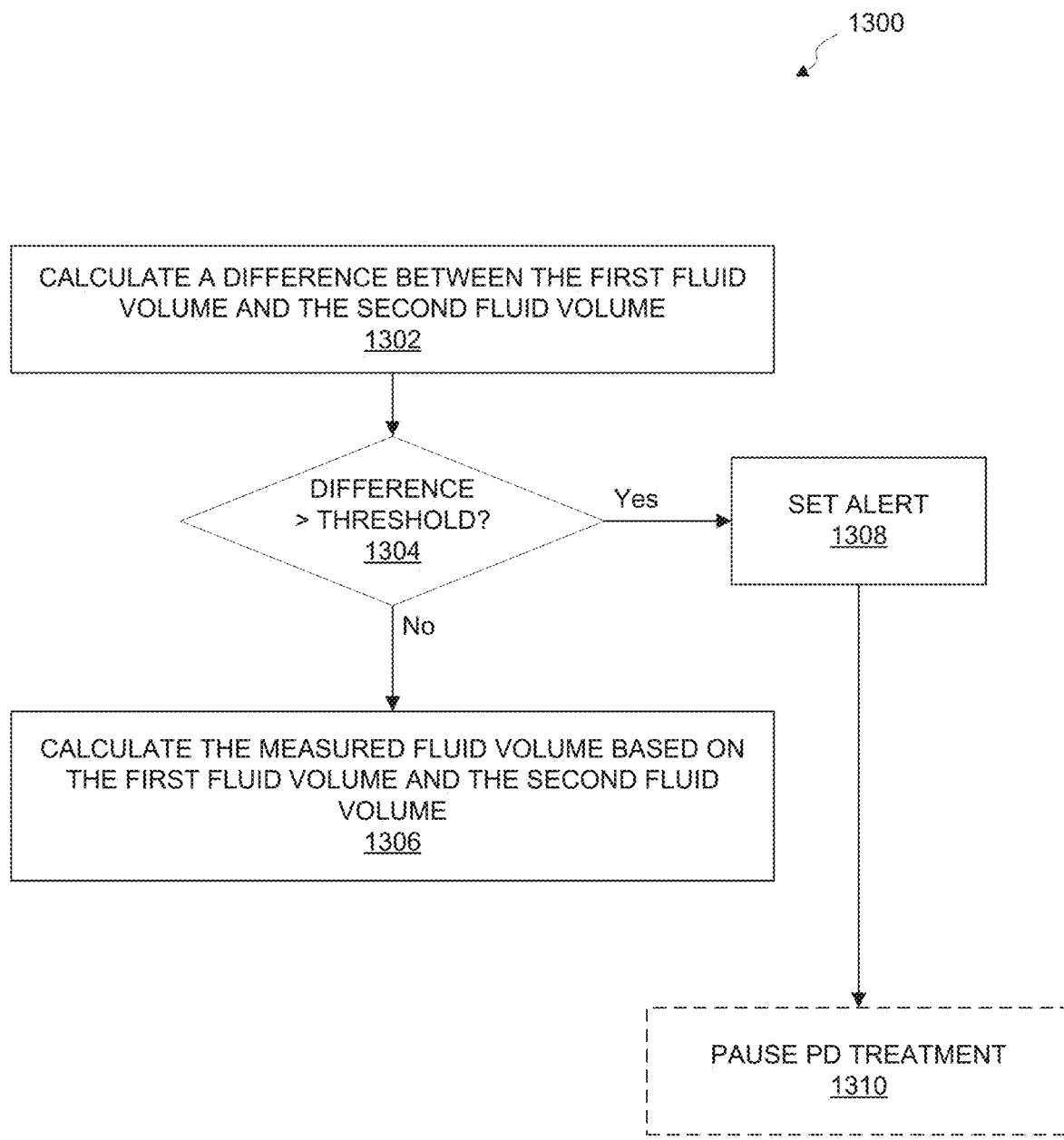
FIG. 13 is a flow diagram of the step for determining a measured fluid volume, in accordance with some embodiments.

FIG. 13 is a flow diagram of method 1300 for determining a measured fluid volume and/or setting an alert, in accordance with some embodiments. In an embodiment, part of the method 1300 can be performed as step 1210 of method 1200, set forth above.

At step 1302, a difference is calculated between the first fluid volume and the second fluid volume. The difference can be indicative of a variance between the two measurements, which can have various causes. For example, manufacturing variations can cause a difference between the volume of the first portion of the cassette 112 and the second portion of the cassette 112. Other causes can include defects in the cassette 112, such as a leak or blockage in the cavities between the first pump chamber 138A and the second pump chamber 138B, or variance in the calibration of the pressure sensor signals.

At step 1304, the difference is compared to a threshold value. In an embodiment, the absolute value of the difference is compared to the threshold value such that the difference is always positive and reflects a magnitude of the disparity between the first fluid volume and the second fluid volume. In some embodiments, the threshold value is a fixed value that is a percentage of the maximum nominal volume of the pump chambers. In other embodiments, the threshold value is dynamically set based on a percentage of the first fluid volume. For example, the threshold value can be set to 10% of the first fluid volume such that the comparison indicates whether the second fluid volume differs from the first fluid volume by more than 10% of the initial measurement.

If the difference is less than the threshold value, then, at step 1306, a measured fluid volume is calculated based on the first fluid volume and the second fluid volume. In an embodiment, the measured fluid volume is calculated by taking a mean of the first fluid volume and the second fluid volume. In another embodiment, the measured fluid volume is calculated by taking the minimum value of the first fluid volume or the second fluid volume. In yet another embodiment, the measured fluid volume is calculated by taking the maximum value of the first fluid volume or the second fluid volume.

Returning to step 1304, if the difference is greater than the threshold value, then, at step 1308, an alert is set. Again, a large disparity in the two independent measurements can be indicative of a possible issue with the cassette 112, fluid lines, or the PD machine 102. In an embodiment, at step 1310, the alert can trigger the PD machine to take a remedial action such as pausing the PD treatment and causing a message to be displayed on the touch screen display 118 of the PD machine 102. The alert may be cleared by the caretaker or patient to continue with the PD treatment.

It will be appreciated that the method 1200 calculates a measured fluid volume for a single pump cycle of the PD machine 102. In some embodiments, the measured fluid volume can be accumulated in a total fluid volume variable to monitor a total amount of fluid drawn from the heater bag line 128. If the control unit 139 determines that the total amount of fluid drawn from the heater bag line is above a threshold value, then the control unit 139 can configure the cassette 112 to withdraw fluid from a second dialysis bag line 126 to transfer additional fluid to the heater bag line 128. In some embodiments, the control unit 139 is configured to measure an amount of fluid transferred to the heater bag line 128 and reduce the total fluid volume variable as fluid is pumped into the heater bag line 128.

Figure 14:
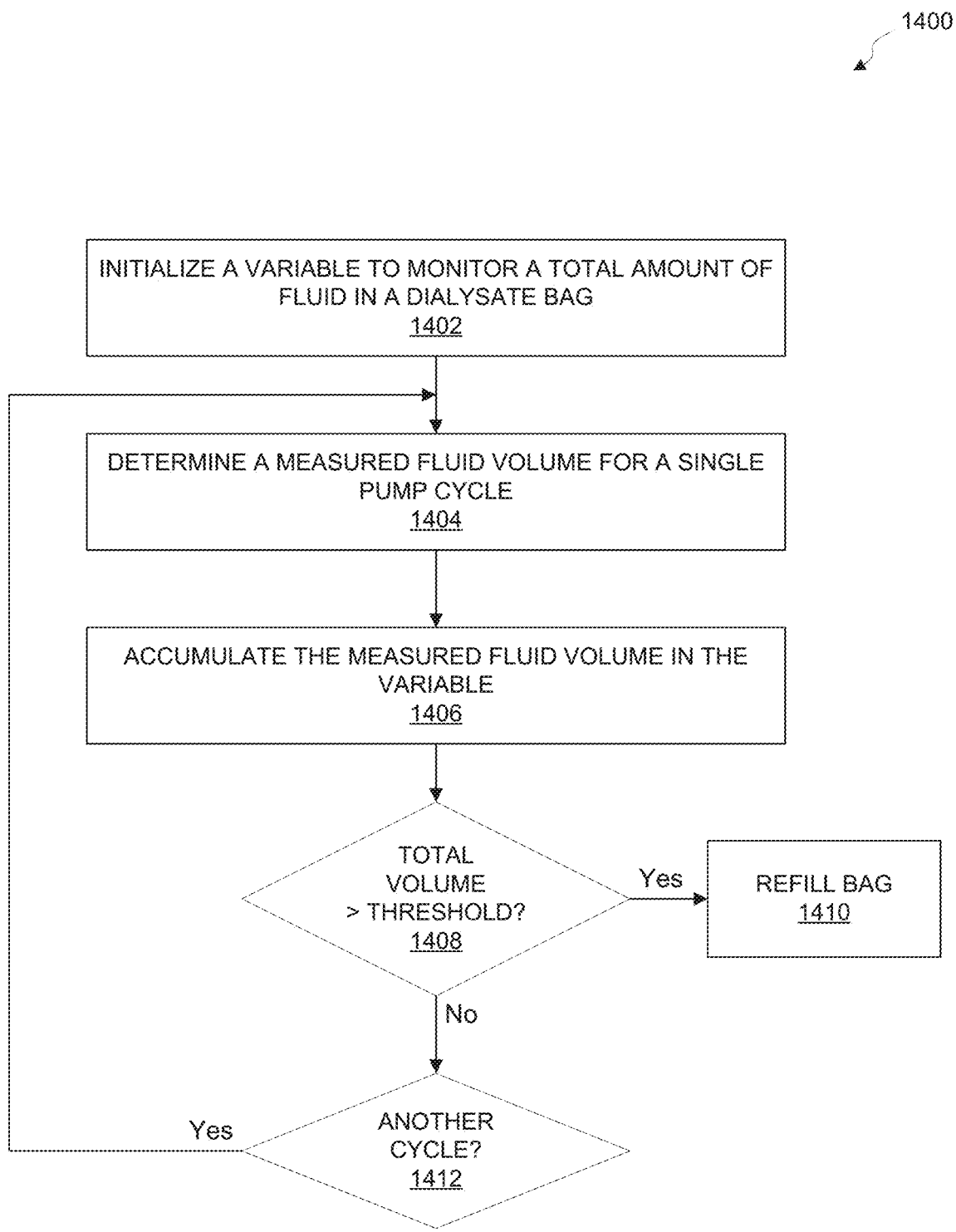
FIG. 14 is a flow diagram of method for monitoring a total fluid volume in a dialysate bag, in accordance with some embodiments.

FIG. 14 is a flow diagram of method 1400 for monitoring a total fluid volume in a dialysate bag, in accordance with some embodiments. It will be appreciated that the method 1400 is described as being performed by the PD system 100. More specifically, the various steps described below can be implemented by a processor, such as the control unit 139 of the PD machine 102, configured to execute a number of instructions. However, it will be appreciated that the method 1400 can be performed by any PD machine configured to drain fluid from a peritoneal cavity of a patient during a PD cycle. In various embodiments, the method 1400 can be implemented using hardware, software executed by a general purpose processor configured to control a specialized apparatus such as a PD machine, or a combination of hardware and software.

At step 1402, a total fluid volume variable is initialized. In an embodiment, the variable can be initialized to store a value of zero. The variable is used to monitor a total amount of fluid drawn from a dialysate bag attached to the PD machine 102. In another embodiment, the variable can be initialized to store a value that reflects an initial volume of fluid in the dialysate bag. The variable is then used to monitor an estimated volume of fluid that remains in the dialysate bag.

At step 1404, a measured fluid volume for a single pump cycle is determined. In an embodiment, step 1404 comprises the method 1200, set forth above.

At step 1406, the measured fluid volume is accumulated into the total fluid volume variable. In an embodiment, the measured fluid volume for the single pump cycle is added to the value stored in the total fluid volume variable. In another embodiment, the measured fluid volume for the single pump cycle is subtracted from the value stored in the total fluid volume variable. The choice of whether to subtract or add the value of the incremental volume for the single pump cycle to the value in the total fluid volume variable is a design choice based on whether the value represents the volume of fluid withdrawn from the dialysate bag or a volume of fluid that remains in the dialysate bag.

At step 1408, the value of the total fluid volume variable is compared to a threshold value. In an embodiment, if the value of the total fluid volume variable is greater than the threshold value, then that indicates that the dialysate bag may be nearly empty and, at step 1410, a refill cycle may be executed to refill the dialysate bag with fluid from a second dialysate bag. However, returning to step 1408, if the value of the total fluid volume variable is less than the threshold value, then that indicates that the dialysate bag may have sufficient fluid to continue a PD treatment and, at step 1412, the PD treatment can continue with another pump cycle returning to step 1404 to continue to accumulate incremental measured fluid volumes for the next pump cycle in the total fluid volume variable. Alternatively, at step 1412, the PD treatment can be discontinued and the total fluid volume variable can be reset for the next PD treatment when new dialysate bags are connected to the PD machine 102.

In another embodiment, at step 1408, if the value of the total fluid volume variable is less than the threshold value, then that indicates that the dialysate bag may be nearly empty. In such an embodiment, the threshold value may be substantially close to zero and the total fluid volume variable may be initialized to a value that represents the initial volume of the dialysate bag, where the incremental measured fluid volume for each pump cycle is subtracted from the total fluid volume variable.

Figure 15:
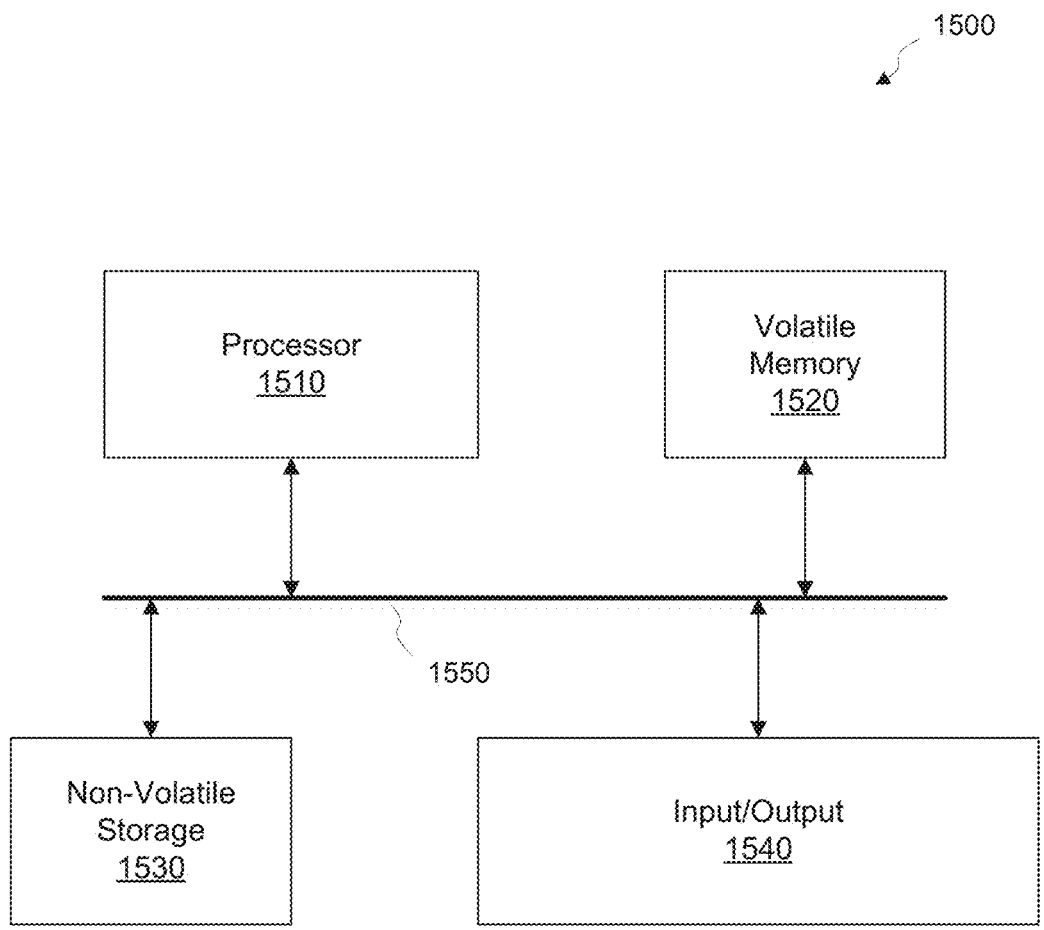
FIG. 15 illustrates an exemplary computer system, in accordance with some embodiments.

FIG. 15 illustrates an exemplary computer system 1500, in accordance with some embodiments. It will be appreciated that, in various embodiments, the control unit 139 can be implemented, at least in part, to include the components of the computer system 1500. The processor 1510 can execute instructions that cause the computer system 1500 to implement the functionality of the control unit 139, as described above.

As depicted in FIG. 15, the system 1500 includes a processor 1510, a volatile memory 1520, a non-volatile storage 1530, and one or more input/output (I/O) devices 1540. Each of the components 1510, 1520, 1530, and 1540 can be interconnected, for example, using a system bus 1550 to enable communications between the components. The processor 1510 is capable of processing instructions for execution within the system 1500. The processor 1510 can be a single-threaded processor, a multi-threaded processor, a vector processor that implements a single-instruction, multiple data (SIMD) architecture, a quantum processor, or the like. The processor 1510 is capable of processing instruction stored in the volatile memory 1520. In some embodiments, the volatile memory 1520 is a dynamic random access memory (DRAM). The instructions can be loaded into the volatile memory 1520 from the non-volatile storage 1530. In some embodiments, the non-volatile storage 1530 can comprise a flash memory such as an EEPROM. In other embodiments, the non-volatile storage 1530 can comprise a hard disk drive (HDD), solid state drive (SSD), or other types of non-volatile media. The processor 1510 is configured to execute the instructions, which cause the PD machine 102 to carry out the various functionality described above.

In some embodiments, the memory 1520 stores information for operation of the PD machine 102. For example, the operating parameters can be stored in the memory 1520. The processor 1510 can read the values of the operating parameters from the memory 1520 and then adjust the operation of the PD machine 102 accordingly. For example, a speed of the pistons 133A, 133B can be stored in or written to the memory 1520 and read from the memory 1520. The speed is then used to control signals transmitted to the stepper motor drivers.

The I/O device(s) 1540 provides input and/or output interfaces for the system 1500. In some embodiments, the I/O device(s) 1540 include a network interface controller (NIC) that enables the system 1500 to communicate with other devices over a network, such as a local area network (LAN) or a wide area network (WAN) such as the Internet. In some embodiments, the non-volatile storage 1530 can include both local and remote computer readable media. The remote computer readable media can refer to a network storage device such as a storage area network (SAN) or a cloud-based storage service. The I/O device(s) 1540 can also include, but are not limited to, a serial communication device (e.g., RS-232 port, USB host, etc.), a wireless interface device (e.g., a transceiver conforming to Wi-Fi or cellular communication protocols), a sensor interface controller, a video controller (e.g., a graphics card), or the like.

It will be appreciated that the system 1500 is merely one exemplary computer architecture and that the control unit 139 or other processing devices can include various modifications such as additional components in lieu of or in addition to the components shown in FIG. 15. For example, in some embodiments, the control unit 139 can be implemented as a system-on-chip (SoC) that includes a primary integrated circuit die containing one or more CPU core, one or more GPU cores, a memory management unit, analog domain logic and the like coupled to a volatile memory such as one or more SDRAM integrated circuit dies stacked on top of the primary integrated circuit dies and connected via wire bonds, micro ball arrays, and the like in a single package (e.g., chip). The chip can be included in a chipset that includes additional chips providing the I/O device 1540 functionality when connected to the SoC via a printed circuit board.

The system and techniques described herein are discussed for illustrative purposes principally in connection with a particular type of PD cycler, for example a PD cycler having piston-based pumps and a heater tray used to batch heat dialysate in a heater bag. It is noted that the system and techniques described herein may be suitably used in connection with other types and configurations of dialysis machines involving the transmission of fluid to and from a patient via a patient line and for which patient line checks and occlusion detection would be beneficially performed. For example, the system and techniques described herein may be used in connection with a PD cycler using a different configuration and style of pump, such as a peristaltic pump, and may be used in connection with other types of dialysate heating arrangements, such as in-line heating arrangements.

It is noted that the techniques described herein may be embodied in executable instructions stored in a computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

What is claimed is:

1. A dialysis system, comprising:
   a plurality of pumps;
   a cassette including a plurality of pump chambers, wherein each pump chamber is fluidly connected to a corresponding pressure chamber; and
   a processor configured to:
   operate a first pump to draw fluid into a first pump chamber fluidly connected to a first pressure chamber,
   measure a first fluid volume in the first pump chamber;
   operate the first pump and a second pump to transfer fluid from the first pump chamber to a second pump chamber fluidly connected to a second pressure chamber,
   measure a second fluid volume in the second pump chamber, and
   determining a measured fluid volume for a single pump cycle based on the first fluid volume and the second fluid volume.

2. The dialysis system of claim 1, wherein each pump comprises a piston configured to engage with a corresponding pump chamber to increase or decrease a volume of the corresponding pump chamber.

3. The dialysis system of claim 2, wherein measuring a fluid volume in the corresponding pump chamber comprises:
   extending the piston to decrease the volume in the corresponding pump chamber;
   monitoring a pressure signal from a pressure transducer configured to measure a fluid pressure in the corresponding pressure chamber;
   reading a position of the piston at a time indicated by the pressure signal; and
   converting the position of the piston into the measured fluid volume.

4. The dialysis system of claim 3, wherein the position of the piston is read based on an encoder signal for a lead screw attached to the piston.

5. The dialysis system of claim 1, wherein determining the measured fluid volume for the single pump cycle comprises:
   determining a difference between the first fluid volume and the second fluid volume;
   comparing the difference to a threshold value; and
   if the difference is below the threshold value, calculating a mean of the first fluid volume and the second fluid volume as the measured fluid volume.

6. The dialysis system of claim 5, wherein determining the measured fluid volume for the single pump cycle further comprises:
   if the difference is above the threshold value, setting an alert.

7. The dialysis system of claim 5, wherein the threshold value is equal to 10 percent of the first fluid volume.

8. The dialysis system of claim 1, wherein the plurality of pumps includes at least three pumps, and wherein the processor is further configured to:
   operate the second pump and a third pump to transfer fluid from the second pump chamber to a third pump chamber fluidly connected to a third pressure chamber;
   measure a third fluid volume in the third pump chamber; and
   calculate a mean of the first fluid volume, the second fluid volume, and the third fluid volume as the measured fluid volume.

9. The dialysis system of claim 1, wherein the fluid is a dialysate solution.

10. The dialysis system of claim 1, wherein fluid is drawn from a heater bag line coupled to the cassette, and wherein the processor is further configured to:
    accumulate the measured fluid volume in a total fluid volume variable to monitor a total amount of fluid drawn from the heater bag line;
    determine that the total amount of fluid drawn from the heater bag line is above a threshold value; and
    configure the cassette to withdraw fluid from a second line to transfer additional fluid to the heater bag line.

11. A method of operating a dialysis machine, the method comprising:
    operating a first pump to draw fluid into a first pump chamber of a cassette, wherein the first pump chamber is fluidly connected to a first pressure chamber;
    measuring a first fluid volume in the first pump chamber;
    operating the first pump and a second pump to transfer fluid from the first pump chamber to a second pump chamber of the cassette, wherein the second pump chamber is fluidly connected to a second pressure chamber;
    measuring a second fluid volume in the second pump chamber; and
    determining a measured fluid volume for a single pump cycle based on the first fluid volume and the second fluid volume.

12. The method of claim 11, wherein each pump chamber is engaged with a piston configured to increase or decrease a volume of the corresponding pump chamber.

13. The method of claim 12, wherein measuring a fluid volume in the corresponding pump chamber comprises:
    extending the piston to decrease the volume in the corresponding pump chamber;
    monitoring a pressure signal from a pressure transducer configured to measure a fluid pressure in the corresponding pressure chamber;
    reading a position of the piston at a time indicated by the pressure signal; and
    converting the position of the piston into the measured fluid volume.

14. The method of claim 11, wherein determining the measured fluid volume for the single pump cycle comprises:
    determining a difference between the first fluid volume and the second fluid volume;
    comparing the difference to a threshold value; and
    if the difference is below the threshold value, calculating a mean of the first fluid volume and the second fluid volume as the measured fluid volume.

15. The method of claim 14, wherein determining the measured fluid volume for the single pump cycle further comprises:
    if the difference is above the threshold value, setting an alert.

16. The method of claim 11, the method further comprising:
    accumulating the measured fluid volume in a total fluid volume variable to monitor a total amount of fluid drawn from a heater bag line;
    determining that the total amount of fluid drawn from the heater bag line is above a threshold value; and configuring the cassette to withdraw fluid from a second line to transfer additional fluid to the heater bag line.

17. A non-transitory computer readable storage medium storing instructions that, when executed by a processor, causes a dialysis machine to measure a fluid volume by performing steps comprising:
operating a first pump to draw fluid into a first pump chamber of a cassette, wherein the first pump chamber is fluidly connected to a first pressure chamber;
measuring a first fluid volume in the first pump chamber;
operating the first pump and a second pump to transfer fluid from the first pump chamber to a second pump chamber of the cassette, wherein the second pump chamber is fluidly connected to a second pressure chamber;
measuring a second fluid volume in the second pump chamber; and
determining a measured fluid volume for a single pump cycle based on the first fluid volume and the second fluid volume.

18. The non-transitory computer readable storage medium of claim 17, wherein each pump chamber is engaged with a piston configured to increase or decrease a volume of the corresponding pump chamber, and wherein measuring a fluid volume in the corresponding pump chamber comprises:
extending the piston to decrease the volume in the corresponding pump chamber;
monitoring a pressure signal from a pressure transducer configured to measure a fluid pressure in the corresponding pressure chamber;
reading a position of the piston at a time indicated by the pressure signal; and
converting the position of the piston into the measured fluid volume.

19. The non-transitory computer readable storage medium of claim 17, wherein determining the measured fluid volume for the single pump cycle comprises:
determining a difference between the first fluid volume and the second fluid volume;
comparing the difference to a threshold value; and
if the difference is below the threshold value, calculating a mean of the first fluid volume and the second fluid volume as the measured fluid volume.

20. The non-transitory computer readable storage medium of claim 17, the steps further comprising:
accumulating the measured fluid volume in a total fluid volume variable to monitor a total amount of fluid drawn from a heater bag line;
determining that the total amount of fluid drawn from the heater bag line is above a threshold value; and
configuring the cassette to withdraw fluid from a second line to transfer additional fluid to the heater bag line.

* * * * *